(12) United States Patent
Trobridge et al.

(10) Patent No.: US 10,036,039 B2
(45) Date of Patent: Jul. 31, 2018

(54) COCAL VESICULOVIRUS ENVELOPE PSEUDOTYPED RETROVIRAL VECTORS

(71) Applicant: Fred Hutchinson Cancer Research Center, Seattle, WA (US)

(72) Inventors: Grant D. Trobridge, Lake Forest Park, WA (US); Hans-Peter Kiem, Seattle, WA (US)

(73) Assignee: FRED HUTCHINSON CANCER RESEARCH CENTER, Seattle, WA (US)

( * ) Notice: Subject to any disclaimer, the term of this patent is extended or adjusted under 35 U.S.C. 154(b) by 0 days.

(21) Appl. No.: 15/684,837

(22) Filed: Aug. 23, 2017

(65) Prior Publication Data

US 2018/0066282 A1     Mar. 8, 2018

Related U.S. Application Data

(60) Continuation of application No. 15/099,939, filed on Apr. 15, 2016, now abandoned, which is a division of application No. 13/318,532, filed as application No. PCT/US2010/033616 on May 4, 2010, now abandoned.

(60) Provisional application No. 61/175,376, filed on May 4, 2009.

(51) Int. Cl.

| | |
|---|---|
| *A61K 39/21* | (2006.01) |
| *A61K 39/12* | (2006.01) |
| *A61K 39/205* | (2006.01) |
| *C12N 15/86* | (2006.01) |
| *C12N 7/00* | (2006.01) |
| *A61K 35/28* | (2015.01) |
| *C07K 14/005* | (2006.01) |
| *A61K 35/12* | (2015.01) |
| *A61K 48/00* | (2006.01) |

(52) U.S. Cl.
CPC .............. *C12N 15/86* (2013.01); *A61K 35/28* (2013.01); *C07K 14/005* (2013.01); *A61K 48/00* (2013.01); *A61K 2035/124* (2013.01); *C12N 2740/16043* (2013.01); *C12N 2740/16045* (2013.01); *C12N 2760/20222* (2013.01); *C12N 2760/20243* (2013.01); *C12N 2810/6081* (2013.01)

(58) Field of Classification Search
CPC .......... C12N 15/86; C12N 2740/15034; C12N 2740/15022; A61K 2039/5256; A61K 39/12
See application file for complete search history.

(56) References Cited

U.S. PATENT DOCUMENTS

2005/0069929 A1    3/2005   Chestnut et al.

FOREIGN PATENT DOCUMENTS

| EP | 2047861 A1 | 4/2009 |
|---|---|---|
| WO | WO200202783 | 1/2002 |
| WO | WO2008115199 A2 | 9/2008 |
| WO | WO2009019612 A2 | 2/2009 |

OTHER PUBLICATIONS

Bhella, et al., "Structure, Expression, and Phylogenetic Analysis of the Glycoprotein Gene of Cocal Virus," Virus Research, vol. 54, 1998, pp. 197-205.
Di Nunzio, et al., "Transduction of Human Hematopoietic Stem Cells by Lentiviral Vectors Psuedotyped with the RD114-TR Chimeric Envelope Glycoprotein," Hum Gene Therapy, vol. 18, No. 9, 2007, pp. 811-820.
Office Action dated Mar. 23, 2017 for U.S. Appl. No. 15/099,939.
Search Reported dated Nov. 12, 2010 in International Application No. PCT/US2010/033616.
Trobridge, et al., "Cocal-pseudotyped Lentiviral Vectors Resist Inactivation by Human Serum and Efficiently Transduce Drimate Hematopoietic Repopulating Cells," Molecular Therapy, vol. 18, No. 4, 2010, pp. 725-733.
Office Action dated Mar. 22, 2016 in European Application No. 10772729.9.

*Primary Examiner* — Barry A Chestnut
(74) *Attorney, Agent, or Firm* — C. Rachal Winger; Lee & Hayes PLLC

(57) ABSTRACT

Provided herein are Cocal vesiculovirus envelope pseudotyped retroviral vectors that exhibit high titers, broad species and cell-type tropism, and improved serum stability. Disclosed Cocal vesiculovirus envelope pseudotyped retroviral vectors may be suitably employed for gene therapy applications and, in particular, for the ex vivo and in vivo delivery of a gene of interest to a wide variety of target cells.

16 Claims, 15 Drawing Sheets

Figure 6
SEQ ID NO: 1
Nucleotide Sequence of Cocal Virus Glycoprotein G Gene

```
   1    aacagtgatc aactgttcca gattcaacat gaatttccta ctcttgacat ttattgtgtt
  61    gccgttgtgc agccacgcca agttctccat tgtattccct caaagccaaa aaggcaattg
 121    gaagaatgta ccatcatctt accattactg cccttcaagt tcggatcaaa actggcacaa
 181    tgatttgctt ggaatcacaa tgaaagtcaa aatgcccaaa acacacaaag ctattcaagc
 241    agacgggtgg atgtgtcatg ctgccaaatg gatcactacc tgtgactttc gctggtacgg
 301    acccaaatac atcactcact ccattcattc catccagcct acttcagagc agtgtaaaga
 361    aagcatcaag caaacaaaac aaggtacttg gatgagtcct ggcttccctc cacagaactg
 421    cgggtatgca acagtaacag actctgtcgc tgttgtcgtc caagccactc ctcatcatgt
 481    cttggttgat gaatatactg gagaatggat cgactctcaa ttccccaacg ggaaatgtga
 541    aaccgaagag tgcgagaccg tccacaactc taccgtatgg tactctgact acaaagtaac
 601    tggattatgt gacgcaactc tggtagacac agagatcacc ttcttctctg aagatggcaa
 661    aaaagaatct atcgggaagc ccaacacagg ctataggagc aactacttcg cttatgagaa
 721    agggacaaa gtatgtaaaa tgaactactg caagcatgcg ggtgtgaggt tgccttccgg
 781    ggtttggttt gagtttgtgg atcaggatgt ctacgccgcc gccaaacttc cagaatgccc
 841    cgttggtgcc actatctccg ctccgacaca gacctctgtt gacgtaagtc tcattctaga
 901    tgtagagaga attttagatt actctctgtg tcaagagaca tggagcaaga tccggtccaa
 961    acagccagta tccctgttg accttagtta cttggccccc aagaatcctg ggaccggacc
1021    ggcattcaca atcatcaatg gcactctgaa gtactttgag accagataca ttcggattga
1081    tatagacaat ccaatcatct ccaagatggt ggggaaaata agtggcagtc aaacagaacg
1141    agaattgtgg acagagtggt tccctacga gggtgtcgag atagggccaa atgggattct
1201    caaaacccct acaggataca aattcccact cttcatgata ggacacggga tgctagattc
1261    cgacttgcac aagacgtccc aagcagaggt ctttgaacat cctcaccttg cagaagcacc
1321    aaagcagttg ccggaggagg agactttatt ttttggtgac acaggaatct ccaaaaatcc
1381    ggtcgaactg attgaagggt ggtttagtag ttggaagagc actgtagtca ccttttttctt
1441    tgccatagga gtatttatac tactgtatgt agtggccaga attgtgatcg cagtgagata
1501    cagatatcaa ggctcaaata acaaaagaat ttacaatgat attgagatga gcagatttag
1561    aaaatgatga agaccctcag atgattatac atatgtgata tgaaaaaaac taacagtcat
1621    catggacttg aatgacttcg agttgagaca gt
```

Figure 7

SEQ ID NO: 2

Amino Acid Sequence of Cocal Virus Glucoprotein G Encoded by SEQ ID NO: 1

```
MNFLLLTFIVLPLCSHAKFSIVFPQSQKGNWKNVPSSYHYCPSSSDQNWHNDLLGITMKVKMPKTHKAIQADGWM
CHAAKWITTCDFRWYGPKYITHSIHSIQPTSEQCKESIKQTKQGTWMSPGFPPQNCGYATVTDSVAVVVQATPHH
VLVDEYTGEWIDSQFPNGKCETEECETVHNSTVWYSDYKVTGLCDATLVDTEITFFSEDGKKESIGKPNTGYRSN
YFAYEKGDKVCKMNYCKHAGVRLPSGVWFEFVDQDVYAAAKLPECPVGATISAPTQTSVDVSLILDVERILDYSL
CQETWSKIRSKQPVSPVDLSYLAPKNPGTGPAFTIINGTLKYFETRYIRIDIDNPIISKMVGKISGSQTERELWT
EWFPYEGVEIGPNGILKTPTGYKFPLFMIGHGMLDSDLHKTSQAEVFEHPHLAEAPKQLPEEETLFFGDTGISKN
PVELIEGWFSSWKSTVVTFFFAIGVFILLYVVARIVIAVRYRYQGSNNKRIYNDIEMSRFRK
```

Figure 8

SEQ ID NO: 3

Nucleotide Sequence of Codon Optimized Cocal Virus Glycoprotein G Gene

```
ATGAATTTTCTTCTCTTGACCTTTATCGTCCTTCCGCTCTGCAGTCACGCTAAATTTTCG
ATCGTCTTCCCACAGAGTCAGAAGGGCAATTGGAAGAATGTACCGAGTTCATATCATTAT
TGTCCAAGCAGCTCTGATCAAAACTGGCATAACGACCTGCTGGGCATTACCATGAAGGTG
AAAATGCCTAAGACACATAAGGCGATTCAGGCAGACGGGTGGATGTGCCACGCAGCCAAG
TGGATTACAACTTGTGACTTCCGATGGTACGGTCCTAAGTATATTACTCACTCCATACAC
AGCATCCAGCCCACCAGTGAGCAGTGCAAAGAGAGTATCAAGCAGACCAAGCAGGGAACC
TGGATGTCACCTGGCTTTCCACCTCAGAATTGTGGCTATGCAACAGTGACAGACTCAGTG
GCTGTTGTGGTGCAGGCAACCCCCCACCACGTACTCGTTGACGAATATACAGGCGAATGG
ATTGACTCCCAGTTTCCCAACGGTAAATGCGAGACAGAAGAGTGCGAGACTGTGCACAAT
TCAACAGTGTGGTACTCCGATTATAAGGTTACCGGGCTTTGCGACGCCACACTGGTGGAC
ACAGAGATAACGTTTTTTTCCGAAGACGGAAAAAAGGAAAGTATCGGGAAACCCAACACT
GGATACCGGAGCAATTACTTCGCGTATGAGAAGGAGATAAGGTCTGCAAAATGAATTAT
TGCAAACACGCCGGGGTAAGGCTGCCCTCCGGCGTGTGGTTTGAGTTCGTGGACCAGGAC
GTCTACGCAGCCGCCAAATTGCCCGAGTGTCCAGTGGGAGCTACAATTTCCGCACCGACA
CAAACCTCAGTGGATGTGTCTCTGATTCTGGACGTAGAGAGGATCCTCGACTACTCTTTG
TGTCAGGAGACGTGGAGCAAGATACGGTCTAAGCAACCAGTCTCACCCGTAGATTTGAGC
TACCTCGCCCCGAAAAACCCAGGCACGGGCCCAGCGTTCACGATCATCAACGGCACGCTT
AAATATTTCGAGACTCGCTATATCCGCATCGACATCGACAATCCTATCATCTCTAAGATG
GTGGGTAAGATCTCTGGATCCCAGACTGAACGAGAACTGTGGACAGAATGGTTCCCCTAC
GAGGGCGTCGAGATTGGCCCTAACGGAATACTGAAGACCCCTACCGGCTATAAGTTCCCT
CTGTTTATGATCGGCCACGGAATGCTGGATTCTGATTTGCATAAGACTTCACAAGCAGAA
GTCTTTGAACATCCTCACCTCGCCGAAGCACCTAAACAGTTGCCTGAGGAAGAGACCCTG
TTCTTCGGCGATACAGGTATATCCAAAAACCCGGTGGAGCTTATCGAAGGTTGGTTTAGC
AGCTGGAAGTCAACAGTGGTAACTTTCTTCTTCGCCATCGGCGTGTTTATACTTCTGTAC
GTAGTGGCCCGCATCGTGATCGCAGTGCGCTACAGATACCAAGGAAGCAACAACAAAAGA
ATCTACAACGACATAGAGATGAGCCGCTTCAGGAAGTGA
```

Figure 9

SEQ ID NO: 4

Amino Acid Sequence of Cocal Virus Glucoprotein G Encoded by SEQ ID NO: 3

```
MNFLLLTFIVLPLCSHAKFSIVFPQSQKGNWKNVPSSYHYCPSSSDQNWHNDLLGITMKV
KMPKTHKAIQADGWMCHAAKWITTCDFRWYGPKYITHSIHSIQPTSEQCKESIKQTKQGT
WMSPGFPPQNCGYATVTDSVAVVVQATPHHVLVDEYTGEWIDSQFPNGKCETEECETVHN
STVWYSDYKVTGLCDATLVDTEITFFSEDGKKESIGKPNTGYRSNYFAYEKGDKVCKMNY
CKHAGVRLPSGVWFEFVDQDVYAAAKLPECPVGATISAPTQTSVDVSLILDVERILDYSL
CQETWSKIRSKQPVSPVDLSYLAPKNPGTGPAFTIINGTLKYFETRYIRIDIDNPIISKM
VGKISGSQTERELWTEWFPYEGVEIGPNGILKTPTGYKFPLFMIGHGMLDSDLHKTSQAE
VFEHPHLAEAPKQLPEEETLFFGDTGISKNPVELIEGWFSSWKSTVVTFFFAIGVFILLY
VVARIVIAVRYRYQGSNNKRIYNDIEMSRFRK
```

Figure 10

SEQ ID NO: 5

Sequence of Cocal vector plasmid pMD2.CocalG

```
GGATCCCCTGAGGGGGCCCCCATGGGCTAGAGGATCCGGCCTCGGCCTCT
GCATAAATAAAAAAAATTAGTCAGCCATGAGCTTGGCCCATTGCATACGT
TGTATCCATATCATAATATGTACATTTATATTGGCTCATGTCCAACATTA
CCGCCATGTTGACATTGATTATTGACTAGTTATTAATAGTAATCAATTAC
GGGGTCATTAGTTCATAGCCCATATATGGAGTTCCGCGTTACATAACTTA
CGGTAAATGGCCCGCCTGGCTGACCGCCCAACGACCCCCGCCCATTGACG
TCAATAATGACGTATGTTCCCATAGTAACGCCAATAGGGACTTTCCATTG
ACGTCAATGGGTGGAGTATTTACGGTAAACTGCCCACTTGGCAGTACATC
AAGTGTATCATATGCCAAGTACGCCCCCTATTGACGTCAATGACGGTAAA
TGGCCCGCCTGGCATTATGCCCAGTACATGACCTTATGGGACTTTCCTAC
TTGGCAGTACATCTACGTATTAGTCATCGCTATTACCATGGTGATGCGGT
TTTGGCAGTACATCAATGGGCGTGGATAGCGGTTTGACTCACGGGGATTT
CCAAGTCTCCACCCCATTGACGTCAATGGGAGTTTGTTTTGGCACCAAAA
TCAACGGGACTTTCCAAAATGTCGTAACAACTCCGCCCCATTGACGCAAA
TGGGCGGTAGGCGTGTACGGTGGGAGGTCTATATAAGCAGAGCTCGTTTA
GTGAACCGTCAGATCGCCTGGAGACGCCATCCACGCTGTTTTGACCTCCA
TAGAAGACACCGGGACCGATCCAGCCTCCCCTCGAAGCTTACATGTGGTA
CCGAGCTCGGATCCTGAGAACTTCAGGGTGAGTCTATGGGACCCTTGATG
TTTTCTTTCCCCTTCTTTTCTATGGTTAAGTTCATGTCATAGGAAGGGGA
GAAGTAACAGGGTACACATATTGACCAAATCAGGGTAATTTTGCATTTGT
AATTTTAAAAAATGCTTTCTTCTTTTAATATACTTTTTTGTTTATCTTAT
TTCTAATACTTTCCCTAATCTCTTTCTTTCAGGGCAATAATGATACAATG
TATCATGCCTCTTTGCACCATTCTAAAGAATAACAGTGATAATTTCTGGG
TTAAGGCAATAGCAATATTTCTGCATATAAATATTTCTGCATATAAATTG
TAACTGATGTAAGAGGTTTCATATTGCTAATAGCAGCTACAATCCAGCTA
CCATTCTGCTTTTATTTTATGGTTGGGATAAGGCTGGATTATTCTGAGTC
CAAGCTAGGCCCTTTTGCTAATCATGTTCATACCTCTTATCTTCCTCCCA
CAGCTCCTGGGCAACGTGCTGGTCTGTGTGCTGGCCCATCACTTTGGCAA
AGCACGTGAGATCTGAATTCATCGATGCGGCCGCCACCATGAATTTTCTT
CTCTTGACCTTTATCGTCCTTCCGCTCTGCAGTCACGCTAAATTTTCGAT
CGTCTTCCCACAGAGTCAGAAGGGCAATTGGAAGAATGTACCGAGTTCAT
ATCATTATTGTCCAAGCAGCTCTGATCAAAACTGGCATAACGACCTGCTG
GGCATTACCATGAAGGTGAAAATGCCTAAGACACATAAGGCGATTCAGGC
AGACGGGTGGATGTGCCACGCAGCCAAGTGGATTACAACTTGTGACTTCC
GATGGTACGGTCCTAAGTATATTACTCACTCCATACACAGCATCCAGCCC
ACCAGTGAGCAGTGCAAAGAGAGTATCAAGCAGACCAAGCAGGGAACCTG
```

Figure 10 Cont'd

```
GATGTCACCTGGCTTTCCACCTCAGAATTGTGGCTATGCAACAGTGACAG
ACTCAGTGGCTGTTGTGGTGCAGGCAACCCCCCACCACGTACTCGTTGAC
GAATATACAGGCGAATGGATTGACTCCCAGTTTCCCAACGGTAAATGCGA
GACAGAAGAGTGCGAGACTGTGCACAATTCAACAGTGTGGTACTCCGATT
ATAAGGTTACCGGGCTTTGCGACGCCACACTGGTGGACACAGAGATAACG
TTTTTTTCCGAAGACGGAAAAAAGGAAAGTATCGGGAAACCCAACACTGG
ATACCGGAGCAATTACTTCGCGTATGAGAAAGGAGATAAGGTCTGCAAAA
TGAATTATTGCAAACACGCCGGGGTAAGGCTGCCCTCCGGCGTGTGGTTT
GAGTTCGTGGACCAGGACGTCTACGCAGCCGCCAAATTGCCCGAGTGTCC
AGTGGGAGCTACAATTTCCGCACCGACACAAACCTCAGTGGATGTGTCTC
TGATTCTGGACGTAGAGAGGATCCTCGACTACTCTTTGTGTCAGGAGACG
TGGAGCAAGATACGGTCTAAGCAACCAGTCTCACCCGTAGATTTGAGCTA
CCTCGCCCCGAAAAACCCAGGCACGGGCCCAGCGTTCACGATCATCAACG
GCACGCTTAAATATTTCGAGACTCGCTATATCCGCATCGACATCGACAAT
CCTATCATCTCTAAGATGGTGGGTAAGATCTCTGGATCCCAGACTGAACG
AGAACTGTGGACAGAATGGTTCCCCTACGAGGGCGTCGAGATTGGCCCTA
ACGGAATACTGAAGACCCCTACCGGCTATAAGTTCCCTCTGTTTATGATC
GGCCACGGAATGCTGGATTCTGATTTGCATAAGACTTCACAAGCAGAAGT
CTTTGAACATCCTCACCTCGCCGAAGCACCTAAACAGTTGCCTGAGGAAG
AGACCCTGTTCTTCGGCGATACAGGTATATCCAAAAACCCGGTGGAGCTT
ATCGAAGGTTGGTTTAGCAGCTGGAAGTCAACAGTGGTAACTTTCTTCTT
CGCCATCGGCGTGTTTATACTTCTGTACGTAGTGGCCCGCATCGTGATCG
CAGTGCGCTACAGATACCAAGGAAGCAACAACAAAAGAATCTACAACGAC
ATAGAGATGAGCCGCTTCAGGAAGTGAAGGCCTGAATTCACCCCACCAGT
GCAGGCTGCCTATCAGAAAGTGGTGGCTGGTGTGGCTAATGCCCTGGCCC
ACAAGTTTCACTAAGCTCGCTTCCTTGCTGTCCAATTTCTATTAAAGGTT
CCTTGGTTCCCTAAGTCCAACTACTAAACTGGGGGATATTATGAAGGGCC
TTGAGCATCTGGATTCTGCCTAATAAAAAACATTTATTTTCATTGCAATG
ATGTATTTAAATTATTTCTGAATATTTTACTAAAAAGGGAATGTGGGAGG
TCAGTGCATTTAAAACATAAAGAAATGAAGAGCTAGTTCAAACCTTGGGA
AAATACACTATATCTTAAACTCCATGAAAGAAGGTGAGGCTGCAAACAGC
TAATGCACATTGGCAACAGCCCTGATGCCTATGCCTTATTCATCCCTCAG
AAAAGGATTCAAGTAGAGGCTTGATTTGGAGGTTAAAGTTTGGCTATGCT
GTATTTTACATTACTTATTGTTTTAGCTGTCCTCATGAATGTCTTTTCAC
TACCCATTTGCTTATCCTGCATCTCTCAGCCTTGACTCCACTCAGTTCTC
TTGCTTAGAGATACCACCTTTCCCCTGAAGTGTTCCTTCCATGTTTTACG
GCGAGATGGTTTCTCCTCGCCTGGCCACTCAGCCTTAGTTGTCTCTGTTG
TCTTATAGAGGTCTACTTGAAGAAGGAAAAACAGGGGGCATGGTTTGACT
GTCCTGTGAGCCCTTCTTCCCTGCCTCCCCCACTCACAGTGACCCGGAAT
CCCTCGACATGGCAGTCTAGCACTAGTGCGGCCGCAGATCTGCTTCCTCG
CTCACTGACTCGCTGCGCTCGGTCGTTCGGCTGCGGCGAGCGGTATCAGC
```

Figure 10 Cont'd

```
TCACTCAAAGGCGGTAATACGGTTATCCACAGAATCAGGGGATAACGCAG
GAAAGAACATGTGAGCAAAAGGCCAGCAAAAGGCCAGGAACCGTAAAAAG
GCCGCGTTGCTGGCGTTTTTCCATAGGCTCCGCCCCCTGACGAGCATCA
CAAAAATCGACGCTCAAGTCAGAGGTGGCGAAACCCGACAGGACTATAAA
GATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGT
GGCGCTTTCTCAATGCTCACGCTGTAGGTATCTCAGTTCGGTGTAGGTCG
TTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGA
CTTATCGCCACTGGCAGCAGCCACTGGTAACAGGATTAGCAGAGCGAGGT
ATGTAGGCGGTGCTACAGAGTTCTTGAAGTGGTGGCCTAACTACGGCTAC
ACTAGAAGGACAGTATTTGGTATCTGCGCTCTGCTGAAGCCAGTTACCTT
CGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGA
TCTCAAGAAGATCCTTTGATCTTTTCTACGGGGTCTGACGCTCAGTGGAA
CGAAAACTCACGTTAAGGGATTTTGGTCATGAGATTATCAAAAAGGATCT
TCACCTAGATCCTTTTAAATTAAAAATGAAGTTTTAAATCAATCTAAAGT
ATATATGAGTAAACTTGGTCTGACAGTTACCAATGCTTAATCAGTGAGGC
ACCTATCTCAGCGATCTGTCTATTTCGTTCATCCATAGTTGCCTGACTCC
CCGTCGTGTAGATAACTACGATACGGGAGGGCTTACCATCTGGCCCCAGT
GCTGCAATGATACCGCGAGACCCACGCTCACCGGCTCCAGATTTATCAGC
AATAAACCAGCCAGCCGGAAGGGCCGAGCGCAGAAGTGGTCCTGCAACTT
TATCCGCCTCCATCCAGTCTATTAATTGTTGCCGGGAAGCTAGAGTAAGT
AGTTCGCCAGTTAATAGTTTGCGCAACGTTGTTGCCATTGCTACAGGCAT
CGTGGTGTCACGCTCGTCGTTTGGTATGGCTTCATTCAGCTCCGGTTCCC
AACGATCAAGGCGAGTTACATGATCCCCCATGTTGTGCAAAAAAGCGGTT
AGCTCCTTCGGTCCTCCGATCGTTGTCAGAAGTAAGTTGGCCGCAGTGTT
ATCACTCATGGTTATGGCAGCACTGCATAATTCTCTTACTGTCATGCCAT
CCGTAAGATGCTTTTCTGTGACTGGTGAGTACTCAACCAAGTCATTCTGA
GAATAGTGTATGCGGCGACCGAGTTGCTCTTGCCCGGCGTCAATACGGGA
TAATACCGCGCCACATAGCAGAACTTTAAAAGTGCTCATCATTGGAAAAC
GTTCTTCGGGGCGAAAACTCTCAAGGATCTTACCGCTGTTGAGATCCAGT
TCGATGTAACCCACTCGTGCACCCAACTGATCTTCAGCATCTTTTACTTT
CACCAGCGTTTCTGGGTGAGCAAAAACAGGAAGGCAAAATGCCGCAAAAA
AGGGAATAAGGGCGACACGGAAATGTTGAATACTCATACTCTTCCTTTTT
CAATATTATTGAAGCATTTATCAGGGTTATTGTCTCATGAGCGGATACAT
ATTTGAATGTATTTAGAAAAATAAACAAATAGGGGTTCCGCGCACATTTC
CCCGAAAAGTGCCACCTGACGT
```

Figure S1. Gammaretroviral pseudotyping

Figure S2. Efficient production of lentiviral vectors from 293C cells

COCAL VESICULOVIRUS ENVELOPE PSEUDOTYPED RETROVIRAL VECTORS

CROSS-REFERENCE TO RELATED APPLICATIONS

This application is a continuation of U.S. Non-Provisional patent application Ser. No. 15/099,939, filed on Apr. 15, 2016, which is a divisional of U.S. Non-Provisional patent application Ser. No. 13/318,532, filed on Mar. 12, 2012, which is a U.S. National Phase of PCT/US2010/033616, filed on May 4, 2010, which claims the benefit of U.S. Provisional Patent Application No. 61/175,376, filed May 4, 2009, all of which are incorporated by reference in their entirety herein.

GOVERNMENT SPONSORED RESEARCH OR DEVELOPMENT

This invention was made with government support under HL036444, HL074162, HL053750, DK077806, DK056465, DK047754, A1063959, and A1061839, awarded by the National Institutes of Health. The government has certain rights in the invention.

SEQUENCE LISTING

The present application includes a Sequence Listing in electronic format as a txt file titled "Sequence_Listing_04May10," which was created on May 4, 2010 and which has a size of 21 kilobytes (KB). The contents of txt file "Sequence_Listing_04May10" are incorporated by reference herein.

BACKGROUND OF THE DISCLOSURE

Technical Field of the Disclosure

The present disclosure relates, generally, to the fields of virology, immunology, and molecular biology. More specifically, provided herein are Cocal vesiculovirus envelope pseudotyped retroviral vectors and particles that exhibit high titers, broad species and cell-type tropism, and improved serum stability. The presently disclosed Cocal vesiculovirus envelope pseudotyped retroviral vectors and particles may be suitably employed for gene therapy applications and, in particular, for the ex vivo and in vivo delivery of a gene of interest to a wide variety of target cells.

Description of the Related Art

Retroviral vectors, in particular lentiviral vectors, have shown great promise for gene therapy in preclinical animal models and more recently also in clinical studies.

Lentiviral vectors have several advantages over gammaretroviral vectors including the ability to more efficiently transduce quiescent cells. Lewis et al., *EMBO J* 11:3053-3058 (1992). This is thought to be due to their ability to enter the nucleus independently of mitosis, but other differences may also be involved. Yamashita and Emerman, Virology 344:88-93 (2006). Lentiviral vectors based on human, simian, or feline immunodeficiency virus can transduce a variety of non-dividing target cells. Case et al., *Proc. Natl. Acad. Sci. U.S.A.* 96:2988-2993 (1999) and Reiser et al., *Proc. Natl. Acad. Sci. U.S.A.* 93:15266-15271 (1996). And, in contrast to gammaretroviral vectors, lentiviral vectors do not typically integrate very close to promoter regions. Schroder et al., *Cell* 110:521-529 (2002). This feature of lentiviral vectors is important for the safe application of gene therapy given the recent occurrences of leukemia in SCID-XI patients treated with gammaretroviral vectors. Hacein-Bey-Abina et al., *Science* 302(5645):415-419 (2003) [erratum *Science* 302(5645):568 (2003)]. In particular, self-inactivating (SIN) lentiviral vectors are likely to have an improved safety profile (Montini et al., *Nat. Biotech.* 24:687-696 (2006)) and can be produced at high titer, which are important considerations when translating gene therapy approaches into the clinic.

Lentiviral vectors and other retroviral vectors are most commonly pseudotyped with Vesicular Stomatitis Virus envelope glycoprotein (VSV-G), which confers a broad tropism and also allows for efficient concentration by centrifugation. Burns et al., *Proc. Natl. Acad. Sci. U.S.A.* 90:8033-8037 (1993). VSV-G pseudotyped lentiviral vectors have shown efficacy for gene transfer to a wide variety of tissues including liver, muscle, brain, kidney, retina, and hematopoietic cells. High levels of gene transfer to hematopoietic repopulating cells have been obtained in large animal models using VSV-G pseudotyped HIV-I based lentiviral vectors (Trobridge et al., *Blood* 111:5537-5543 (2008) and Horn et al., *Blood* 103:3710-3716 (2004)), and HIV-based lentiviral vectors are currently being used for clinical trials for hematopoietic stem cell (HSC) gene therapy.

There are, however, some disadvantages to using VSV-G to pseudotype retroviral vectors. Toxicity is associated with the constitutive expression of VSV-G, which has made generation of stable packaging cell lines difficult (Ory et al., *Proc. Natl. Acad. Sci. U.S.A.* 93:11400-11406 (1996)) and vectors pseudotyped with the VSV-G envelope glycoprotein are inactivated by human serum complement (DePolo et al., *Mol. Ther.* 2_:218-222 (2000)), which may limit the use of VSV-G pseudotyped lentiviral vectors for gene therapy applications where the vector is delivered in vivo.

Alternate pseudotypes have been evaluated including the Feline Endogeneous Virus (RDI 14) glycoprotein which has shown promise for HSC gene transfer. Sandrin et al. developed an RD 114-based envelope glycoprotein with a modified transmembrane-region (RD 114/TR) that allows for efficient pseudotyping of lentiviral vectors and also allows for efficient concentration of lentiviral vectors by centrifugation. *Blood* 100:823-832 (2002). RD114/TR pseudotyped vectors mediate efficient gene transfer into human hematopoietic progenitors and NOD/SCID repopulating cells (Di Nunzio et al., *Hum. Gene Ther:* 811-820 (2007)) and RD114 pseudotyped vectors also mediate efficient gene transfer in large animal models. Neff et al., *Mol. Ther.* 2:157-159 (2004); Hu et al., *Mol. Ther:* 611-617 (2003); and Kelly et al., *Blood Cells, Molecules, & Diseases* 30:132-143 (2003). RD114 pseudotyped vectors are also resistant to human serum complement (Cosset et al., *J Virol.* 69:7430-7436 (1995) and Sandrin et al., *Blood* 100:823-832 (2002)), and RD114 pseudotyped oncoretroviral vectors have been used for in vivo delivery in the canine X-SCID model. Ting-De Ravin et al., *Blood* 107:3091-3097 (2006). The titers reported for RD 114/TR pseudotyped lentiviral vectors have, however, generally been lower than those obtained with VSV-G, which may limit their utility for clinical gene therapy applications.

Cocal virus is in the Vesiculovirus genus, and is a causative agent of vesicular stomatitis in mammals. Cocal virus was originally isolated from mites in Trinidad (Jonkers et al., *Am. J Vet. Res.* 25:236-242 (1964)), and infections have been identified in Trinidad, Brazil, and Argentina from insects, cattle, and horses. Many of the vesiculoviruses that infect mammals have been isolated from naturally infected arthropods, suggesting that they are vector-borne. Antibodies to vesiculoviruses are common among people living in rural areas where the viruses are endemic and laboratory-acquired; infections in humans usually result in influenza-like symptoms. The Cocal virus envelope glycoprotein shares 71.5% identity at the amino acid level with VSV-G Indiana, and phylogenetic comparison of the envelope gene of vesiculoviruses shows that Cocal virus is serologically distinct from, but most closely related to, VSV-G Indiana strains among the vesiculoviruses. Jonkers et al., *Am. J Vet. Res.* 25:236-242 (1964) and Travassos da Rosa et al., *Am. J Tropical Med. & Hygiene* 33:999-1006 (1984).

There remains an unmet need in the art for improved retroviral vectors that may be generated in sufficiently high titers to permit their use in ex vivo and in vivo gene therapy applications, that exhibit broad species and cell-type tropism, and that are resistant to serum degradation in vivo.

SUMMARY OF THE INVENTION

The present invention addresses these and other related needs by providing, inter alia, Cocal vesiculovirus envelope pseudotyped retroviral vector particles that may be suitably employed for gene transfer applications including gene therapy and vaccines, and, in particular, for the ex vivo and in vivo delivery of a gene of interest to a wide variety of target cells. The Cocal vesiculovirus envelope pseudotyped retroviral vector particles disclosed herein exhibit high titers, broad species and cell-type tropism, and improved serum stability.

Thus, within certain embodiments, the present disclosure provides Cocal vesiculovirus envelope pseudotyped retroviral vector particles including, for example, lentiviral, alpharetroviral, betaretroviral, gammaretroviral, deltaretroviral, and epsilonretroviral vector particles that comprise retroviral Gag, Pol, and/or one or more accessory protein(s) and a Cocal vesiculovirus envelope protein. Within certain aspects of these embodiments, the Gag, Pol, and accessory proteins are lentiviral and/or gammaretroviral. Within other aspects, the Cocal vesiculovirus envelope protein is encoded by a polynucleotide comprising the nucleotide sequence of SEQ ID NO: 1 and has the amino acid sequence presented in SEQ ID NO: 2. Within yet other aspects, the Cocal vesiculovirus envelope protein is encoded by a polynucleotide comprising a nucleotide sequence that is human codon-optimized such as, for example, the nucleotide sequence of SEQ ID NO: 3. One such Cocal vesiculovirus envelope protein encoded by a human codon-optimized polynucleotide is exemplified by the amino acid sequence of SEQ ID NO: 4.

Within other embodiments, the present disclosure provides polynucleotides comprising a human codon-optimized nucleotide sequence encoding a Cocal vesiculovirus envelope protein. An exemplary human codon-optimized nucleotide sequence is presented as SEQ ID NO: 3, which sequence encodes the Cocal vesiculovirus envelope protein having the amino acid sequence of SEQ ID NO: 4.

Still further embodiments of the present disclosure provide plasmid vectors for the expression of a Cocal vesiculovirus envelope protein, which vectors comprise a polynucleotide encoding a Cocal vesiculovirus envelope protein wherein the polynucleotide is under the transcriptional control of a eukaryotic transcriptional promoter. Exemplary polynucleotides that encode a Cocal vesiculovirus envelope protein include the nucleotide sequence of SEQ ID NO: 1, which encodes the protein having the amino acid sequence of SEQ ID NO: 2, as well as a human codon-optimized variant of that nucleotide sequence that is presented as SEQ ID NO: 3 and which encodes the amino acid sequence of SEQ ID NO: 4. An exemplary plasmid vector for the expression of a Cocal vesiculovirus envelope proteins is designated herein as pMD2.CocalG, which has the nucleotide sequence presented as SEQ ID NO: 5.

Other embodiments provide Cocal vesiculovirus envelope proteins, in particular proteins encoded by human codon-optimized nucleotide sequences. An exemplary Cocal vesiculovirus envelope protein of the present disclosure has the amino acid sequence of SEQ ID NO: 4, which may be encoded by the nucleotide sequence of SEQ ID NO: 3.

Yet other embodiments of the present disclosure provide methods for generating Cocal envelope pseudotyped retroviral vector particles, which methods comprise the step of transfecting a cell with a retroviral vector plasmid, a retroviral helper plasmid or plasmids, and a plasmid vector for the expression of a Cocal vesiculovirus envelope protein. Exemplified herein are methods for generating Cocal envelope pseudotyped retroviral vector particles wherein the retroviral vector plasmids and retroviral helper plasmids are lentiviral vector plasmids and lentiviral helper plasmids. Also exemplified herein, are methods for generating Cocal envelope pseudotyped retroviral vector particles wherein the retroviral vector plasmids and retroviral helper plasmids are gammaretroviral vector plasmids and gammaretroviral helper plasmids. It will be understood, however, that other Cocal envelope pseudotyped retroviral vector particles including, for example, alpharetroviral, betaretroviral, deltaretroviral, and epsilonretroviral vector particles may also be generated by the presently disclosed methods by employing suitable vector and helper plasmids that are known to those of skill in the art.

Further embodiments of the present disclosure provide methods for delivering a gene of interest to a target cell, which methods comprise the step of contacting a target cell with a Cocal vesiculovirus envelope pseudotyped retroviral vector particle.

Still further embodiments of the present disclosure provide methods for delivering a gene of interest into a hematopoietic system of a patient, which methods comprise the steps of: (a) harvesting CD34+ hematopoietic stem cells (HSCs) from the patient; (b) transducing the HSCs ex vivo with a Cocal vesiculovirus envelope pseudotyped retroviral vector particle comprising the gene of interest; and (c) introducing the ex vivo transduced HSCs into the patient under conditions that allow reconstitution of the patient's hematopoietic system.

The present disclosure also provides methods for identifying a patient susceptible to treatment with a Cocal vesiculovirus envelope pseudotyped retroviral vector particle, which methods comprise the steps of: (a) isolating a serum sample from the patient; (b) contacting the Cocal vesiculovirus envelope pseudotyped retroviral vector particle with the serum sample; and (c) testing the Cocal vesiculovirus envelope pseudotyped retroviral vector particle for serum inactivation.

These and other aspects of the present invention will become apparent upon reference to the following detailed description and attached drawings. All publications, patents, and patent applications cited herein, whether supra or infra, are hereby incorporated by reference in their entirety.

BRIEF DESCRIPTION OF THE FIGURES

FIG. 6. Nucleotide sequence of Cocal vesiculovirus envelope glycoprotein (GenBank Accession No. AF045556; SEQ ID NO: 1).

FIG. 7. Amino acid sequence of Cocal vesiculovirus envelope glycoprotein (SEQ ID NO: 2) encoded by the nucleotide sequence of FIG. 6 (SEQ ID NO: 1).

FIG. 8. Nucleotide sequence of the human codon enriched Cocal vesiculovirus envelope glycoprotein (SEQ ID NO: 3) based on the nucleotide sequence of FIG. 6 (SEQ ID NO: 1).

FIG. 9. Amino acid sequence of human codon enriched Cocal vesiculovirus envelope glycoprotein (SEQ ID NO: 4) encoded by the nucleotide sequence of FIG. 8 (SEQ ID NO: 3).

FIG. 10. Nucleotide sequence of the lentiviral vector designated pMD2.CocalG (SEQ ID NO: 5).

DETAILED DESCRIPTION OF THE DISCLOSURE

Figure 1:
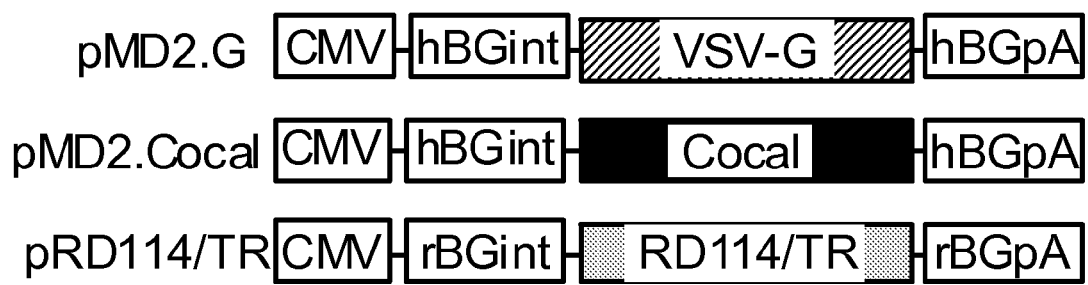
FIG. 1. Envelope plasmids. All envelopes were expressed from a CMV promoter with a human or rabbit beta globin intron (hBGint, rBGint) 5' to the ORF and a human or rabbit beta globin poly A sequence (hBGpA, rBGpA). The Cocal ORF was codon-optimized for human cells.
Figure 2:
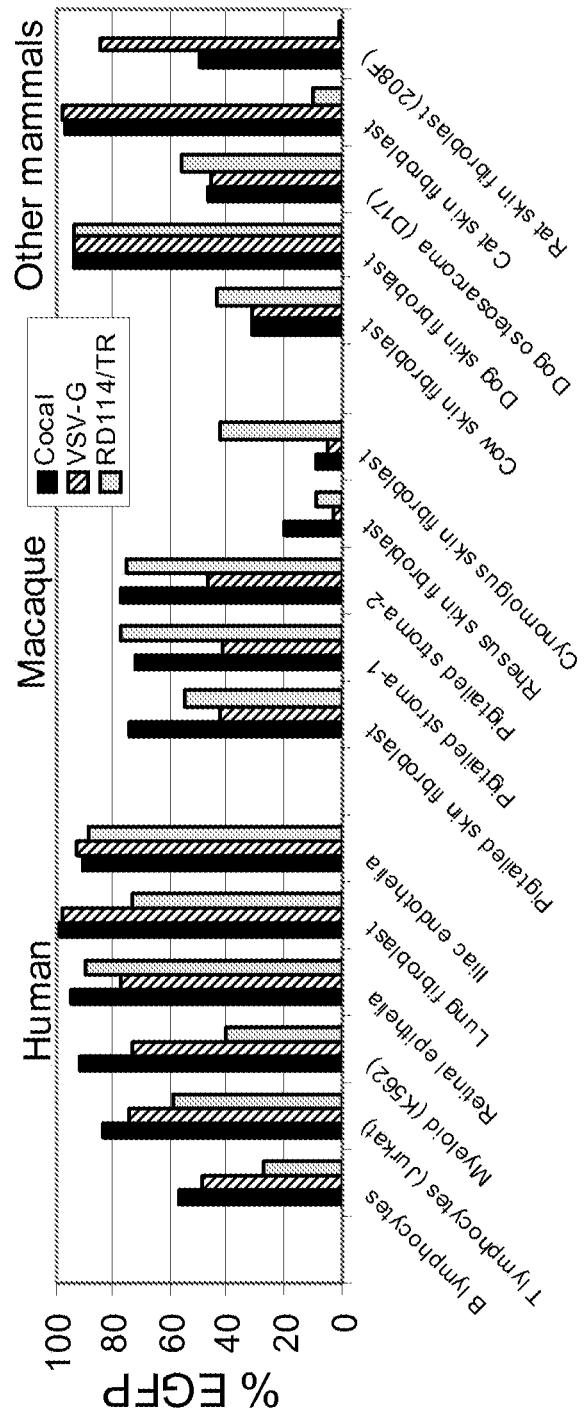
FIG. 2. Tropism of Cocal envelope relative to VSV-G and RD 114/TR envelopes. The indicated cell lines and primary cell cultures were transduced at an MOI of 5 and the percentage of Enhanced Green Fluorescent Protein (EGFP)-expressing cells was determined 6 days after vector exposure.

As indicated above, the present disclosure is based on the discovery that retroviral vectors may be efficiently pseudotyped using the Cocal vesiculovirus envelope glycoprotein described by Bhella et al., *Virus Res.* 54:197-205 (1998), and that Cocal vesiculovirus envelope glycoprotein pseudotyped retroviral vectors can be produced at high titer, are stable to ultracentrifugation and repeated freeze-thaw cycles, exhibit broad species and cell-type tropism, can efficiently transduce long-term repopulating cells in a clinically relevant nonhuman primate model, are resistant to serum inactivation, and are less susceptible to in vivo immune responses in patients. Thus, the Cocal vesiculovirus envelope glycoprotein pseudotyped retroviral vectors disclosed herein will find broad utility in gene therapy applications including, for example, the transduction of hematopoietic progenitor or stem cells for the in vivo repopulation of a patient's hematopoietic cell system.

The present disclosure is exemplified by specific reference to Cocal pseudotyped lentiviral vectors and Cocal pseudotyped gammaretroviral vectors. It will be understood, that the teachings disclosed herein may be extended with routine experimentation to the pseudotyping of other viral vectors derived from other enveloped viruses, in particular, viral vectors derived from the range of alternative retroviruses including alpharetroviral, betaretroviral, deltaretroviral, and epsilonretroviral. The present disclosure further contemplates that the Cocal envelope may be employed to pseudotype a wide variety of enveloped vectors that can be pseudotyped with VSV-G such as, for example, VSV vectors, baculovirus vectors, and hybrid alphavirus/rhabdovirus vectors. Rose et al., *Proc. Natl. Acad. Sci. USA.* 105(15): 5839-43 (2008); Rose et al., *8th Conj. Retrovir. Oppor. Infect:* 50 (2001); Cooper et al., *J Viral:* 207-19 (2008); Li et al., *J Gene Med.* 11(2):150-9 (2009); and Li et al., *J Gene Med.* 11(1):57-65 (2009). It is further contemplated that the Cocal envelope pseudotyped vectors disclosed herein may be superior for certain vaccine applications due to reduced serum neutralization.

VSV-G is the most commonly used envelope used to pseudotype lentiviral vectors due to its broad tropism and biophysical properties that allow for generation of vector virions at high titer that are stable during ultracentrifugation and freeze-thawing. One drawback of VSV-G pseudotyped lentiviral vectors, that is overcome by the presently disclosed Cocal envelope pseudotyped lentiviral vectors, is that human serum can inactivate VSV-G pseudotyped virions thereby limiting their utility for in vivo delivery. DePolo et al., *Mal. Ther.* 2_:218-222 (2000) and Croyle et al., *J Viral.* 78:912-921 (2004). Also, humans develop potent immune responses against VSV-G after the administration of VSV-G vector transduced cells which can limit the efficacy of future infusions of VSV-G pseudotyped vectors.

As disclosed herein, quite surprisingly, the Cocal vesiculovirus envelope glycoprotein allows for efficient HIV-based lentiviral pseudotyping and gene transfer and confers stability during ultracentrifugation and multiple freeze-thaw cycles. Lentiviral vectors may be reproducibly generated and concentrated to over $10^8$ TU per ml. Cocal glycoprotein envelope exhibits a broad tropism and mediates efficient transduction of human cell types from all tissues and species tested. Cocal envelope is efficacious for gene delivery to several important therapeutic target cell types including skin fibroblasts, stroma, and hematopoietic progenitors and can efficiently transduce a clinically relevant nonhuman primate competitive repopulation model. Lentiviral vectors pseudotyped with Cocal virus glycoprotein are less sensitive to neutralization by human serum, as compared to lentiviral vectors pseudotyped with VSV and RD 114/TR envelope glycoproteins, and exhibit utility for in vivo gene delivery applications.

In summary, the present disclosure provides a novel pseudotype for production of lentiviral vectors that can be efficiently concentrated to very high titers and that also demonstrated efficient transduction of several cell types important for gene therapy including primate hematopoietic repopulating cells. Cocal pseudotyped lentiviral vectors will be useful for many therapeutic gene transfer applications and may be particularly useful for in vivo delivery in humans due to their resistance to inactivation by human serum.

Each of these embodiments of the present invention is described in further detail herein below.

The practice of the present invention will employ, unless indicated specifically to the contrary, conventional methods of virology and immunology within the skill of the art, many of which are described below for the purpose of illustration. Such techniques are explained fully in the literature. See, e.g., Fields et al., "Virology" (3rd Edition, 1996); Sambrook, et al., "Molecular Cloning: A Laboratory Manual" (2nd Edition, 1989); "DNA Cloning: A Practical Approach, vol. I & II" (D. Glover, ed.); "Oligonucleotide Synthesis" (N. Gait, ed., 1984); "Nucleic Acid Hybridization" (B. Hames & S. Higgins, eds., 1985); Perbal, "A Practical Guide to Molecular Cloning" (1984); Ausubel et al., "Current Protocols in Molecular Biology" (New York, John Wiley and Sons, 1987); Bonifacino et al., "Current Protocols in Cell Biology" (New York, John Wiley & Sons, 1999); Coligan et al., "Current Protocols in Immunology" (New York, John Wiley & Sons, 1999); Harlow and Lane *Antibodies: a Laboratory Manual* Cold Spring Harbor Laboratory (1988); and Lo, Ed., "Antibody Engineering: Methods and Protocols," Part 1 (Humana Press, Totowa, N.J. 2004). Techniques for producing both types of mutations are well known in the art. For example, specific mutations can be introduced using site-specific mutagenesis as described in Sambrook et al., "Protocols in Molecular Biology," supra. Random mutations in specific regions can be introduced using, for example, forced evolution as described in Gulick and Fahl, *Proc. Natl. Acad. Sci. USA,* 92:8140-8144 (1995).

As used in this specification and the appended claims, the singular forms "a," "an" and "the" include plural references unless the context clearly dictates otherwise.

Cocal Vesiculovirus Envelope Pseudotyped Retroviral Vector Particles

As indicated above, the present disclosure is directed to Cocal vesiculovirus envelope pseudotyped retroviral vector particles, including, for example, lentiviral vector particles and gammaretroviral particles, that exhibit high titers, broad species and cell-type tropism, and improved serum stability and, as a consequence, may be suitably employed for gene therapy applications and, in particular, for the ex vivo and in vivo delivery of a gene of interest to a wide variety of target cells.

The Cocal vesiculovirus envelope pseudotyped lentiviral vector particles disclosed herein comprise lentiviral Gag, Pol, and one or more accessory protein(s) and a Cocal vesiculovirus envelope protein. Exemplified herein are Cocal vesiculovirus envelope pseudotyped lentiviral vector particles wherein the envelope protein (SEQ ID NO: 2) is encoded by a polynucleotide comprising the nucleotide sequence of SEQ ID NO: 1, as well as envelope proteins encoded by human codon-optimized nucleotide sequences such as, for example, the nucleotide sequence of SEQ ID NO: 3. One such Cocal vesiculovirus envelope protein encoded by a human codon-optimized polynucleotide is exemplified by the amino acid sequence of SEQ ID NO: 4. Cocal envelope pseudotyped lentiviral vector particles described herein typically result in concentrated titers of at least $10^6$, $10^7$, $10^8$, or $10^9$ transducing units (TU)/ml.

Species and cell-type tropism of the Cocal envelope pseudotyped lentiviral vector particles may be determined by transducing a wide variety of cell cultures such as, for example, Epstein-Barr virus transformed human B-lymphocytes, SV40-transformed fetus-derived human retinal epithelia, SV40-transformed human iliac artery-derived endothelial cells, untransformed *Macaca nemestrina* skin fibroblasts, untransformed *Macaca mulatta* skin fibroblasts, untransformed *Macaca fascicularis* skin fibroblasts, untransformed *Bos taurus* skin fibroblasts, untransformed *Canisfamiliaris* skin fibroblasts, untransformed *Felis catus* skin fibroblasts, human IMR90 cells, D17 canine osteosarcoma cells, 208F embryo fibroblasts, human Jurkat cells, K562 myelogenous leukemia cells, and macaque stromal cells.

Serum stability of the Cocal envelope pseudotyped lentiviral vector particles may be determined by mixing vector particle preparations with serum at 37° C. for 30 minutes followed by addition to HT 1080 cells. Gene transfer was evaluated by flow cytometry for expression of a gene of interest 3 days after vector particle exposure, and determining the percentage of cells expressing the gene of interest after incubation in the serum relative to the percentage of cells expressing the gene of interest in a vector-only control to determine the fold increase or decrease in titer after exposure to serum.

Plasmid Vectors Comprising a Polynucleotide Encoding a Cocal Vesiculovirus Envelope Protein Still further embodiments of the present disclosure provide plasmid vectors for the expression of Cocal vesiculovirus envelope proteins, which vectors comprise a polynucleotide encoding a Cocal vesiculovirus envelope protein wherein the polynucleotide is under the transcriptional control of a eukaryotic transcriptional promoter. Exemplary polynucleotides that encode a Cocal vesiculovirus envelope protein include the nucleotide sequence of SEQ ID NO: 1 (GenBank Accession No. AF045556), which encodes the protein having the amino acid sequence of SEQ ID NO: 2, as well as a human codon-optimized variant of that nucleotide sequence that is presented as SEQ ID NO: 3 and which encodes the amino acid sequence of SEQ ID NO: 4.

An exemplary plasmid vector for the expression of a Cocal vesiculovirus envelope proteins is designated herein as pMD2.CocalG, which has the nucleotide sequence presented as SEQ ID NO: 5. The pMD2.CocalG plasmid is derived from the pMD2.G described by Didier Trono and that is available from Addgene (Cambridge, Mass., Plasmid No. 12259). More specifically, the pMD2.CocalG plasmid was generated by removing the VSV-G coding sequence from the pMD2.G plasmid and ligating a polynucleotide encoding a Cocal vesiculovirus envelope protein between the human-globin intron and polyadenylation sequences and downstream of the constitutively active CMV promoter. In the case of the pMD2.CocalG plasmid described herein, the polynucleotide encoding the Cocal vesiculovirus envelope protein was first human codon-optimized using GeneMaker technology (Blue Heron Biotechnology, Bothell, Wash.). It will be understood that this exemplary polynucleotide (SEQ ID NO: 3) is representative of a wide range of human codon-optimized polynucleotides that may be employed in the presently disclosed plasmid vectors for the expression of a Cocal vesiculovirus envelope protein.

Cocal Vesiculovirus Envelope Proteins

Cocal vesiculovirus envelope proteins have been described in the literature (see, for example, Bhella et al., *Virus Res.* 54:197-205 (1998) and GenBank Accession No. AF045556). The present disclosure also provides Cocal vesiculovirus envelope proteins encoded by human codon-optimized nucleotide sequences. An exemplary Cocal vesiculovirus envelope protein of the present disclosure has the amino acid sequence of SEQ ID NO: 4, which may be encoded by the human codon-optimized nucleotide sequence of SEQ ID NO: 3.

Methods for Generating Cocal Envelope Pseudotyped Retroviral Vector Particles

The present disclosure provides methods for generating Cocal envelope pseudotyped retroviral vector particles that comprise the step of transfecting a cell with a retroviral vector plasmid, a retroviral helper plasmid, and a plasmid vector for the expression of a Cocal vesiculovirus envelope protein. Exemplified herein are methods for generating Cocal envelope pseudotyped lentiviral vector particles that comprise the step of transfecting a cell with a lentiviral vector plasmid, a lentiviral helper plasmid, and a plasmid vector for the expression of a Cocal vesiculovirus envelope protein. It will be understood by those of skill in the art that these methods may be applied, with routine experimentation, to the generation of Cocal envelope pseudotyped retroviral vector particles including alpharetroviral, betaretroviral, gammaretroviral, deltaretroviral, and epsilonretroviral vector particles.

A wide variety of methodologies are available in the art for the generation of envelope pseudotyped lentiviral vector particles that may be modified by employing a plasmid vector for the expression of a Cocal vesiculovirus envelope protein, as described herein, to achieve Cocal envelope pseudotyped lentiviral vector particles. For example, such lentiviral vector particles may be produced by transient transfection of human cells, such as embryonic kidney (HEK) 293 cells by the calcium phosphate method or by the polyethylenimine (PEI) method with a combination of a lentiviral vector plasmid; a lentiviral helper plasmid; and a Cocal vesiculovirus envelope protein plasmid.

Suitable lentiviral vector plasmids include, for example, the SIN HIV vector plasmids pRRLSIN.cPPT.PGK-GFP-.WPRE (Addgene Plasmid No. 12252) and pRRLSIN.cPPT-.PGK-YFP.WPRE (Naldini, San Raffaele Telethon Institute for Gene Therapy, Italy), both of which contain a central polypurine tract, a woodchuck post-transcriptional regulatory element, and an internal phosphoglycerate kinase (PGK) promoter driving expression of enhanced green fluorescent protein (EGFP) or enhanced yellow fluorescent protein (EYFP). An exemplary helper plasmid is pCMV R8.74 described by Dull et al., *J Virol.* 72:8463-8471 (1998).

Methods Employing Cocal Envelope Pseudotyped Lentiviral Vector Particles

The present disclosure provides methods for delivering a gene of interest to a target cell that comprise the step of contacting a target cell with a Cocal vesiculovirus envelope pseudotyped lentiviral vector particle and entry of the particle.

The present disclosure exemplifies these methods by describing the delivery of a gene of interest into a hematopoietic system of a patient, which methods comprise the steps of: (a) harvesting CD34+ hematopoietic stem cells (HSCs) from the patient; (b) transducing the HSCs ex vivo with a Cocal vesiculovirus envelope pseudotyped lentiviral vector particle comprising the gene of interest; and (c) introducing the ex vivo transduced HSCs into the patient under conditions that allow reconstitution of the patient's hematopoietic system.

Hematopoietic stem cells may be harvested from a patient, transduced ex vivo with Cocal vesiculovirus envelope pseudotyped lentiviral vector particles, then reintroduced to reconstitute the entire hematopoietic system. Human CD34+ cells may be isolated from a patient by harvesting marrow cells, labeling with anti-CD34+ monoclonal antibodies, and separating the CD34+ cells by magnetic beads, such as MACS IgM microbeads (Miltenyi Biotec, Auburn, Calif.) according to the manufacturer's instructions. Trobridge et al., Blood 111:5537-5543 (2008). Human CD34+ cells may be cultured in IMDM with FBS, Flt-3 ligand, stem cell factor, thrombopoietin, interleukin 3, interleukin 6, and granulocyte colony-stimulating factor).

CD34+ cells are typically transduced by pretreatment with CH-296 fibronectin fragment (Takara, New York, N.Y.) and exposed to Cocal vesiculovirus envelope pseudotyped lentiviral vector particles a MOI of 5 for 20 hours. Cells may then be washed, resuspended in medium, and tested for transduction by, for example, CFU analysis or flow cytometry or by PCR analysis. After exposure to vector preparations, the HSCs may be reintroduced into the patient to allow reconstitution of the patient's hematopoietic system.

The present disclosure further provides methods for identifying a patient susceptible to treatment with a Cocal vesiculovirus envelope pseudotyped lentiviral vector particle that comprise the steps of: (a) isolating a serum sample from the patient; (b) contacting the Cocal vesiculovirus envelope pseudotyped lentiviral vector particle with the serum sample; and (c) testing the Cocal vesiculovirus envelope pseudotyped lentiviral vector particle for serum inactivation.

The following Examples are offered by way of illustration, not limitation. The following non-limiting examples are provided to illustrate various aspects of the present disclosure. All references, patents, patent applications, published patent applications, and the like are incorporated by reference in their entireties herein.

EXAMPLES

Example 1

Materials and Methods

Construction of a Cocal Envelope Pseudo Type Plasmid

The deduced open reading frame (ORF) from the published sequence of Cocal envelope (Bhella et al., *Virus Res.* 54:197-205 (1998); GenBank Accession No. AF045556; SEQ ID NO: 1) was used to generate a human codon-optimized polynucleotide (SEQ ID NO: 3) that was synthesized by Blue Heron Biotechnology (Bothell, Wash.) using GeneMaker technology according to the sequence specified with ClaI and StuI flanking restriction sites. The optimized Cocal ORF was subcloned by standard techniques into pMD2.G kindly provided by Didier Trono, Lausanne, Switzerland (Addgene Plasmid No. 12259) replacing the VSV-G ORF to create pMD2.CocalG.

Production of Pseudotyped Lentiviral Vector Preparations and Determination of Titer The SIN HIV vector plasmids used were pRRLSIN. cPPT.PGK-GFP.WPRE (Addgene Plasmid No. 12252) and pRRLSIN.cPPT.PGK-YFP.WPRE (kindly provided by Luigi Naldini, San Raffaele Telethon Institute for Gene Therapy, Italy), which contain a central polypurine tract, a woodchuck post-transcriptional regulatory element, and an internal phosphoglycerate kinase (PGK) promoter driving expression of enhanced green fluorescent protein (EGFP) or enhanced yellow fluorescent protein (EYFP).

HIV-based vector particles were produced by transient transfection of human embryonic kidney (HEK) 293 cells (Graham et al., *J Gen. Virol.* 36:59-74 (1977)) by calcium phosphate method as previously described (Hom et al., *Blood* 103:3710-3716 (2004)) or by polyethylenimine (PEI) method (Boussif et al., *Proc. Natl. Acad. Sci. U.S.A.* 92:7297-7301 (1995)) with 27 µg lentiviral vector plasmid; 17.5 µg lentiviral helper plasmid pCMV R8.74 (Dull et al., *J Virol.* 72:8463-8471 (1998)); and envelope plasmid (3 µg Cocal, 6 µg VSV-G, or 9 µg RD|14/TR)). For polyethylenimine-mediated transfection the plasmid DNA was added to 2 ml of serum-free DMEM and 3 µL of 1 µg/µL PEI (25 kDa Linear Catalog No. 23966 from Polysciences, Inc., Warrington, Pa.) per µg of DNA was added and the solution was immediately mixed by vortexing for 10 seconds and allowed to stand at room temperature for 15 minutes. The solution was then added dropwise to the HEK 293 cells and all subsequent steps were the same as for calcium phosphate-mediated transfection.

Vector particles were concentrated 100-fold by centrifugation for 20-22 hours at 6300 g at 4° C. For freeze-thaw experiments, the vector particles were frozen at −70° C. for 1 hour then placed in a 37° C. water bath until completely thawed and then removed to room temperature. The titer of vector particle preparations was determined by adding vector particle preparations to HEK 293 cells or human HT1080 fibrosarcoma cells (Rasheed et al., *Cancer* 33:1027-1033 (1974)) plated at $1 \times 10^5$ cells/ml the day before vector particle addition. Protamine sulfate was added immediately before addition of vector particle at a final concentration of 8 µg/ml. Transduced cells were assayed by flow cytometry 3-4 days after vector exposure, and the percentage of EGFP-expressing cells was used to calculate the number of EGFP transducing units (TU)/ml of vector preparation.

Evaluation of Cocal Tropism in Cell Lines and Primary Cell Cultures

All cell cultures were supplemented with 10% fetal bovine serum (FBS) and penicillin and streptomycin unless otherwise stated. Epstein-Barr virus transformed human B-lymphocytes (Cat. No. AG09387), SV40-transformed fetus-derived human retinal epithelia (Cat. No. AG06096), SV40-transformed human iliac artery-derived endothelial cells (Cat. No. AG 10427), untransformed *Macaca nemestrina* skin fibroblasts (Cat. No. AG08426), untransformed *Macaca mulatta* skin fibroblasts (Cat. No. AG06249), untransformed *Macaca fascicularis* skin fibroblasts (Cat. No. AG21329), untransformed *Bos taurus* skin fibroblasts (Cat. No. AG08130), untransformed *Canisfamiliaris* skin fibroblasts, and untransformed *Felis catus* skin fibroblasts (Cat. No. GM06207) were obtained from the Coriell Institute for Medical Research (Camden, N.J.) and cultured as directed. Human IMR90 cells were obtained from the American Type Culture Collection (ATCC Cat. No. CCL-186) and cultured in Eagle's Minimum Essential Medium with 15% FBS. D|7 canine osteosarcoma cells (ATCC CRL-6248) and rat 208F embryo fibroblasts (Quade, *Virol.* 98:461-465 (1979)) were cultured in Dulbecco's Modified Eagle Medium (DMEM). Human Jurkat cells were cultured in RPMI-1640. Gillis and Watson, *J Exp. Med.* 152:1709-1719 (1980). K562 myelogenous leukemia cells (Lozzio and Lozzio, *Blood* 45(3):321-334 (1975)) were cultured in Iscove's Modified Dulbecco's Medium (IMDM). Macaque stromal cells were isolated from *Macaca* nemestrina bone marrow aspirates that were depleted of red blood cells by two washes with hemolytic buffer (150 mM ammonium chloride, 12 mM sodium bicarbonate, 0.1 mM EDTA), and nucleated cells were plated at $1 \times 10^6$ to $2 \times 10^6$ cells/ml in tissue culture-treated T-75 flasks and cultured for 3 to 4 weeks in alpha minimum essential medium with 20% FBS and L-glutamine.

For the first 3 days after plating, one-half of the media was replaced in each flask daily, and after the first 3 days, the medium was changed every third day. Cells were passaged once or twice per week upon reaching approximately 80% confluence. The absence of hematopoietic markers was confirmed after 3 to 4 weeks of culture by immunostaining and flow cytometry. For all cell types, cells were plated at $1 \times 10^5$ cells/ml the day before vector addition and vector was added at an MOI of 5 based on the titer on HEK 293 cells. Gene transfer was evaluated by flow cytometry for EGFP expression 6 days after vector exposure.

Serum Neutralization Assays

Human serum samples were obtained under an institutional review board (IRB)-approved protocol at Fred Hutchinson Cancer Research Center and stored frozen at −20° C. prior to use. Dogs were raised and housed at the Fred Hutchinson Cancer Research Center (FHCRC) and macaques were housed at the University of Washington National Primate Research Center under conditions approved by the American Association for Accreditation of Laboratory Animal Care. Twenty µl of serum were mixed with VSV-G, Cocal, or RD 114/TR vector preparations with $5 \times 10^5$ (Coca) and VSV-G) or $5 \times 10^4$ (RD114/TR) EGFP TU in triplicate and incubated at 37° C. for 30 minutes then added to $1 \times 10^5$ HT1080 cells. A vector-only control was also incubated at 37° C. for 30 min.

Gene transfer was evaluated by flow cytometry for EGFP expression 3 days after vector exposure, and the percentage of EGFP-expressing cells after incubation in the serum was determined relative to the percentage of EGFP-expressing cells in the vector-only control to determine the fold increase or decrease in titer after exposure to serum.

Isolation and Transduction o(CD34+ Hematopoietic Progenitors

Human CD34+ cells were collected from a volunteer under an institutional review board approved protocol and isolated by magnetic beads (Miltenyi Biotec, Auburn, Calif.) according to the manufacturer's instructions and stored in liquid nitrogen until use. Bone marrow CD34-enriched primate cells were isolated using the 12.8 IgM anti-CD34+ antibody and MACS IgM microbeads (Miltenyi Biotec, Auburn, Calif., United States) according to the manufacturer's instructions as previously described. Trobridge et al., *Blood* 111:5537-5543 (2008). Canine bone marrow CD34+ were isolated as previously described (Goerner et al., *Blood* 98:2065-2070 (2001) and Neff et al., *Blood* 100:2026-2031 (2002)) using the biotinylated monoclonal antibody 1H6 (IgG 1 anti-canine CD34) and used without cryopreservation.

Human CD34+ cells were thawed and cultured overnight in IMDM with 10% FBS, 100 ng/ml Flt-3 ligand, 100 ng/ml stem cell factor [SCF], 100 ng/ml thrombopoietin [TPO], 100 ng/ml interleukin 3 [IL-3], 100 ng/ml interleukin 6 [IL-6] and 100 ng/ml granulocyte colony-stimulating factor [G-CSF]). $1 \times 10^5$ CD34+ cells were then added to each well of a 24-well plate pretreated with 50 µg/ml CH-296 fibronectin fragment (Takara, New York, N.Y.) and exposed to vector at a MOI of 5 for 20 hours with 4 µg/mL protamine sulfate. Cells were then washed, resuspended in medium, and plated in tissue culture treated 24-well plates or plated for CFU analysis or cultured for 10 days and analyzed by flow cytometry on day 10. For CFU assay CD34-enriched cells (3000 per 35-mm plate) were cultured in a double-layer agar culture system. Briefly, isolated cells were cultured in MEM alpha medium (Invitrogen, Carlsbad, Calif.) supplemented with 25% FBS (Hyclone, Logan, Utah), 0.1% BSA (fraction V; Sigma), ImM L-Glutamine, 50 U/mL penicillin, 50 µg/mL streptomycin and 0.3% (wt/vol) SeaPlaque agarose (Cambrex, East Rutherford, N.J.) overlaid on MEM alpha medium with 0.5% SeaPlaque agarose (wt/vol) containing 100 ng/mL of SCF, MGDF, IL-3, IL-6, granulocyte-macrophage colony-stimulating factor (GM-CSF), G-CSF, 4 U/mL erythropoietin, 25% FBS, 0.1% BSA, 1mM L-Glutamine, 50 U/mL penicillin and 50 µg/mL streptomycin. Cultures were incubated at 37° C. in 5% C02 in a humidified incubator. All CFU cultures were performed in triplicate. The total number, as well as the number of EGFP-positive colonies, was enumerated at day 14 of culture by fluorescence microscopy to determine the percentage of cells expressing the transgene.

CD34-enriched primate cells were thawed and cultured in IMDM with 10% FBS with 100 U/mL penicillin and 100 µg/mL streptomycin, supplemented with 100 ng/mL rhSCF, 100 ng/mL rhuFlt3-L, 100 ng/mL interleukin (IL)-3, 100 ng/mL IL-6, 100 ng/mL TPO, and 100 ng/mL G-CSF for 15-18 hours before transduction. For transduction, cells were supplemented with the same cytokine combination in flasks previously coated with the CH-296 fragment of fibronectin (Retronectin, Takara, Shiga, Japan) and with 4 µg/mL protamine sulfate. The cells were exposed to an initial dose of vector for 16 hours and then exposed to second dose of vector overnight for 8 hours, then washed, resuspended in medium and plated in 24-well plates. The cells were analyzed by flow cytometry for EGFP expression on day 10.

Canine CD34-enriched cells were cultured in IMDM with 10% FBS, 10 U/mL penicillin and 100 µg/mL streptomycin, supplemented with 50 ng/mL canine G-CSF, 50 ng/mL canine SCF, 50 ng/mL rhFlt3-L, and 50 ng/mL rhMGDF. $1 \times 10^5$ freshly isolated CD34+ cells were plated in each well of a 12-well plate pretreated with 50 µg/ml CH-296 fibronectin fragment (Takara, New York, N.Y.) and supplemented with 4 µg/mL protamine sulfate. The cells were exposed to vector in triplicate at an MOI of 5 for 20 hours, then washed, resuspended in medium and plated in 24-well plates and analyzed by flow cytometry on day 10.

Analysis of Marking in the Macaque Model Using a Competitive Repopulation Assay

Macaque CD34+ cells were isolated and transductions were performed as indicated above except that cells were exposed to an initial dose of vector for 6.5-8 hours and then exposed to a second dose of vector overnight for 17-18 hours at an MOI of 20. Following transduction, cells were infused into the recipient after myeloablative total body irradiation (TBI) conditioning. Animal L06348 received a myeloablative dose of 1020 cGy TBI in four doses of 255 cGy, from a single source linear X-ray accelerator (Linac Systems, Inc., Lakewood, N.J., USA) at 7 cGy/minute. After infusion of autologous gene-modified cells, the animals received recombinant G-CSF at 100 µg/kg daily until the animals maintained an ANC of >500/µL. To suppress a potential immune response to the EGFP and EYFP proteins, tacrolimus was orally administered daily at a concentration of 2.5 mg/kg 2 days prior to infusion of vector-exposed cells and continued for 10 days. The concentration was then increased to 3.5 mg/kg until 56 days post-transplant then tapered to 1.2 mg/kg until day 65 post-transplant. The animal also received standard supportive care including intravenous hydration and broad spectrum antibiotics (cetazadime, vancomycin, gentamicin), an antiviral agent (acyclovir), an antifungal agent (fluconazole) and transfusions with irradiated pig-tailed macaque whole blood for treatment of post-transplant thrombocytopenia. Leukocytes were isolated by ammonium chloride red cell lysis from heparinized peripheral blood and bone marrow samples drawn at multiple time points after transplantation were analyzed for EGFP expression on a FACSVantage or FACSCalibur (Becton-Dickinson, San Jose, Calif.). Transgene expression in granulocyte, monocyte, and lymphocyte populations was determined by gating based on either forward and right-angle light scatter characteristics or expression of lineage-specific CD markers. The antibodies used for lineage-specific markers included CD3 (clone SP34-2), CD13 (clone L138), CD20 (clone L27), and CD34 (clone 563). All antibodies were supplied by Becton Dickinson (Franklin Lakes, N.J.) and conjugated to phycoerythrin. Red cells and platelets from whole blood diluted in phosphate-buffered saline were delineated by forward and right-angle light scatter properties and assessed for EGFP or EYFP expression.

Example 2

Construction of a Cocal Expression Plasmid and Pseudotyping of Lentiviral Vectors A human codon optimized version of Cocal DNA was synthesized based on the amino acid sequence reported by Bhella et al., *Virus Research* 54:197-205 (1998). The optimized sequence was cloned into the plasmid backbone that expresses the Cocal envelope glycoprotein from a CMV promoter with a human-globin intron and polyadenylation sequence (FIG. 1). This plasmid backbone is identical to the plasmid backbone for pMD.2G, a VSV-G plasmid routinely used for the production of VSV-G pseudotyped lentiviral vectors.

SIN lentiviral vectors that express the enhanced green fluorescent (EGFP) protein from a phosphoglycerate kinase (PGK) promoter were generated by transient transfection and pseudotyped with Cocal, VSV-G, or RD114/TR envelope. Viral titers were determined on HEK 293 cells and also on human HT1080 fibrosarcoma cells. Protamine sulfate and polybrene are cationic polymers commonly used to enhance infection with retroviruses (Manning et al., *Appl. Microbial.* 22:1162-1163 (1971)) and transduction with retroviral vectors (Cornetta and Anderson, *J. Viral. Methods* 23:187-194 (1989)) including vectors pseudotyped with VSV-G and RD 114/TR. Transduction with and without protamine sulfate were compared using Cocal pseudotyped lentiviral vectors. The addition of protamine sulfate at a concentration of 8 µg/ml enhanced transduction of HT1080 cells approximately seven-fold, so protamine sulfate was included during vector exposure for all subsequent experiments.

When producing VSV-G pseudotyped lentiviral vectors by transient transfection, varying the amount of envelope plasmid can significantly affect titers. Lentiviral vectors were, therefore, prepared that express the enhanced green fluorescent (EGFP) protein with varying amounts of each envelope pseudotype and titers were compared on HEK 293 cells. For all three pseudotypes, titers varied with the amount of envelope glycoprotein used in the transient transfection; titers also varied slightly between different plasmid preparations. High titers were routinely achieved using either 3 µg of Cocal, 6 µg of VSV-G, or 9 µg of the RD114/TR envelope plasmid in a standard transient transfection protocol which also included 27 µg of vector plasmid and 17.5 µg of helper plasmid to transfect $1.2 \times 10^7$ HEK 293 cells. The Cocal envelope plasmid had a human codon-optimized ORF which increased the efficiency of Cocal envelope glycoprotein production in transfected HEK 293 cells.

Vector stocks were prepared in triplicate, concentrated 100-fold by centrifugation, and the titers were compared before and after a single freeze thaw or after 3 freeze-thaw cycles (Table 1).

mediated the most efficient gene transfer, and also in cat and rat fibroblasts where both Cocal and VSV-G pseudotyped vectors mediated much higher transduction efficiencies than the RD 114/TR pseudotype.

TABLE 1

Efficiency of Concentration and Freeze-thaw Stability of Lentiviral Pseudotypes

| Pseudotype | Titer | Concentrated Titer (100X) | Concentration efficiency* | 1X Freeze-thaw efficiency† | 3X Freeze-thaw efficiency† |
|---|---|---|---|---|---|
| Cocal | $5.7 \times 10^6 \pm 3.3 \times 10^5$ | $3.0 \times 10^8 \pm 1.7 \times 10^7$ | 53% ± 3.9% | 94.7% ± 4.1% | 83.5% ± 2.2% |
| VSV-G | $5.8 \times 10^6 \pm 9.2 \times 10^4$ | $3.7 \times 10^8 \pm 2.0 \times 10^7$ | 63.1% ± 2.9% | 85.9% ± 2.6% | 79.3% ± 4.0% |
| RD114/TR | $5.2 \times 10^4 \pm 1.9 \times 10^3$ | $1.3 \times 10^6 \pm 2.1 \times 10^5$ | 24.8% ± 3.1% | 88.7% ± 46.7% | 62.8% ± 16.2% |

*The percent of EGFP transducing units remaining after 100-fold concentration.
†The percent of EGFP transducing units remaining after the indicated number of freeze-thaw cycles.

Lentiviral vectors prepared with either the Cocal or the VSV-G envelope reproducibly resulted in concentrated titers of approximately $10^8$ EGFP transducing units (TU)/ml, while pseudotyping with the RD 114/TR envelope yielded lower titers and was more variable with ranges between $10^6$ and $10^7$ TU/ml. The Cocal envelope allowed for efficient concentration by centrifugation and efficiently retained titer at similar levels to VSV-G during multiple freeze-thaw cycles.

Example 3

Cocal Pseudotyped Lentiviral Vectors have a Broad Tropism

Figure 3:
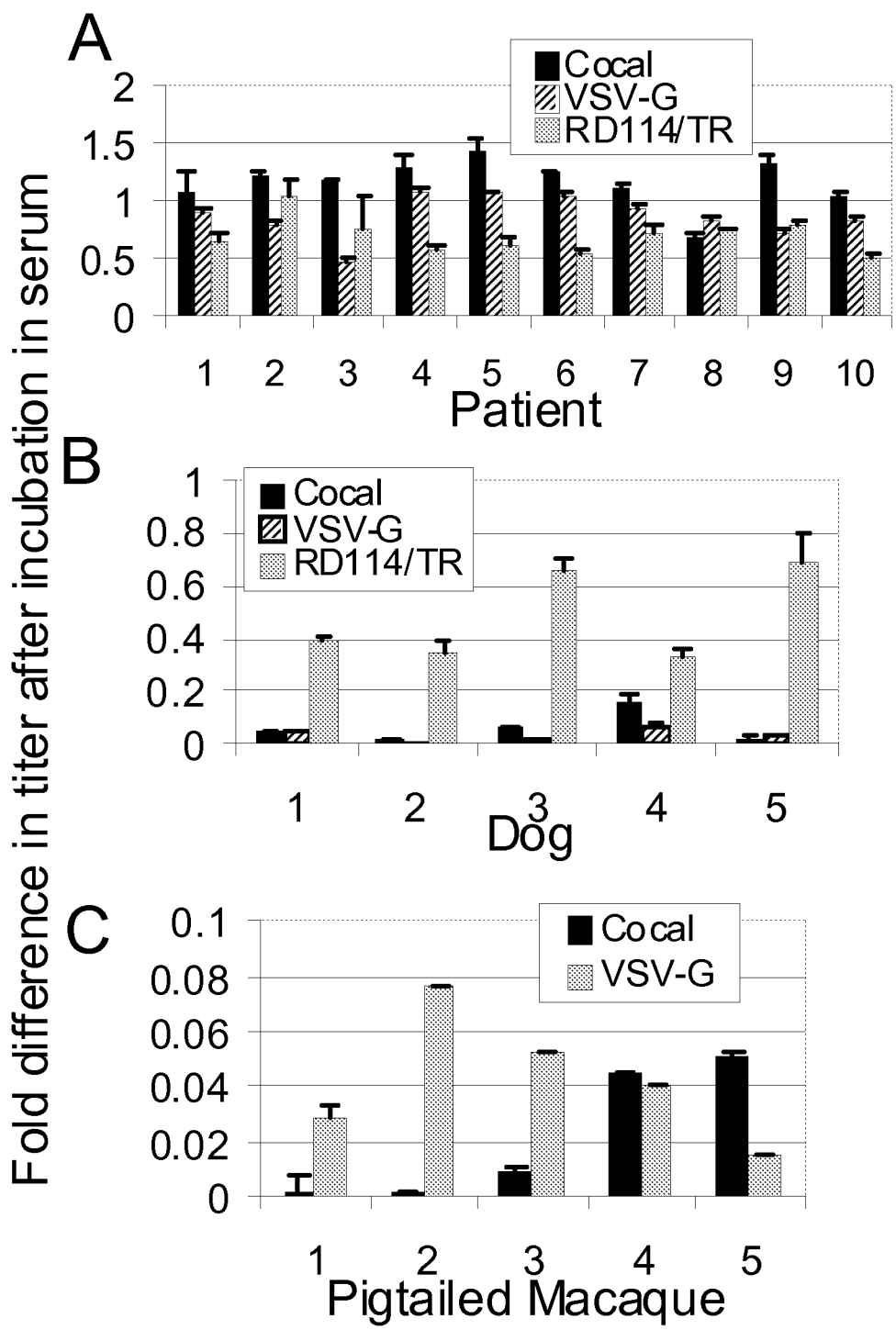
FIG. 3. Serum neutralization of lentiviral pseudotypes. Serum from 10 humans (A), 5 dogs (B), and 5 macaques (C) were incubated with vector at 37° C. for 30 minutes then added to HT1080 cells to evaluate the number of EGFP-transducing units. EGFP expression was evaluated by flow cytometry for EGFP expression 3 days after vector exposure, and the percentage of EGFP expressing cells after incubation in the serum was determined relative to the percentage of EGFP expressing cells in the vector-only control to determine the fold increase or decrease in titer after exposure to serum.
Figure 4:
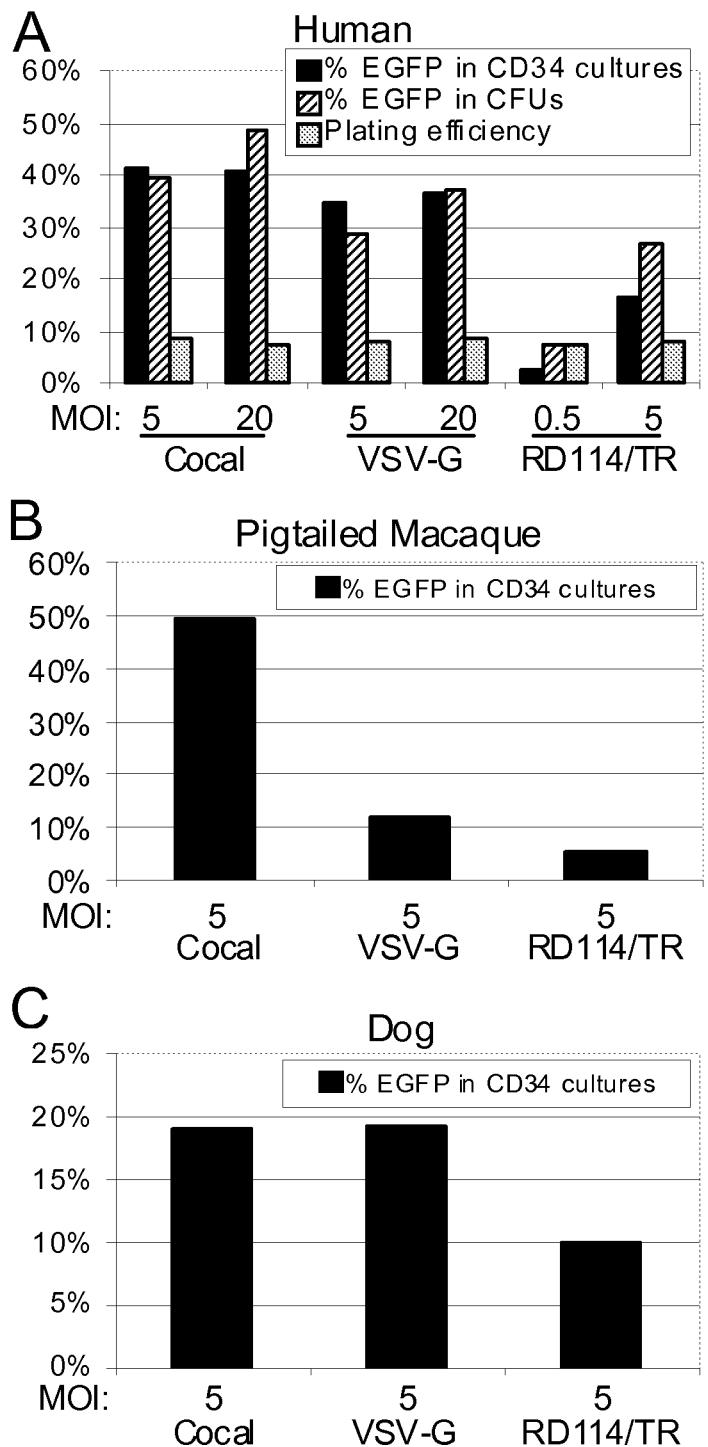
FIG. 4. Comparison of pseudotypes for gene transfer to hematopoietic progenitors. CD34+ cells were exposed to vector at a MOI of 5 or 20 for hours then added to each well of a 24-well plate for CFU analysis. The percentage of EGFP-expressing cells was determined in liquid cultures 10 days after vector exposure by flow cytometry and the percentage of EGFP-expressing CPUs were determined by fluorescent microscopy 14 days after vector exposure.

The high titers of Cocal pseudotyped vector preparations suggested that they will be highly effective for many gene transfer and gene therapy applications. The efficiency of transduction was compared for a panel of cell lines and primary cells derived from several tissues that are important targets for gene therapy, and from several species commonly used as preclinical models for gene therapy. FIG. 3 shows the relative transduction efficiency of transformed human cell lines and primary cells derived from blood, retinal epithelia, lung fibroblasts, bone endothelia, skin fibroblasts, stroma from humans, three species of macaques, cow, dog, cat or rat. The Cocal envelope allowed for highly efficient transduction of cell types from all tissues and most species tested with the exception of rhesus (Macaca mulatta) and cynomolgous or crab-eating macaque (Macaca fascicularis) nonhuman primate cells where the transduction rates were very low for all pseudotypes. This was as expected due to host cell restriction of the HIV-based lentiviral vector transduction by Trim S a. Stremlau et al., Nature 427:848-853 (2004). In pigtailed macaque (Macaca nemestrina) cells, defective Trim5a isoforms (Brennan et al., J Viral. 81(22): 12210-7 (2007)) allows for infection with HIV-I (Agy et al., Science 257:103-106 (1992)) and also for efficient gene transfer with lentiviral vectors. Trobridge et al., Blood 111:5537-5543 (2008).

Overall, gene transfer was similar for Cocal and VSV-G in all tissues and species tested with the exception of macaques, where Cocal envelope mediated higher gene transfer efficiency relative to VSV-G in all five primary cell types tested. The transduction efficiency using Cocal pseudotyped vectors was also similar to RD 114/TR pseudotyped vector except in the cynomolgous or crab-eating macaque (Macaca fascicularis), where RD114/TR Example 4

Cocal Pseudotyped Lentiviral Vectors are Resistant to Human Serum

The high titer, broad tropism, and stability of Cocal pseudotyped lentiviral vectors suggested that will also be highly effective for in vivo delivery of transgenes. One limitation of in vivo gene delivery using VSV-G pseudotyped lentiviral vectors is that in humans, serum neutralization of VSV-G pseudotyped vectors limits their effectiveness.

DePolo et al., Mal. Ther. 2_:218-222 (2000). VSV-G and Cocal vesiculovirus envelope glycoproteins have 71.5% identity at the amino acid level, and VSV-G and Cocal vesiculoviruses are distinct serologically. Jonkers et al., Am. J Vet. Res. 25:236-242 (1964) and Travassos da Rosa et al., Am. J Tropical Med. & Hygiene 33:999-1006 (1984).

The ability of serum from 10 individuals to inactivate lentiviral vector virions produced using each pseudotype. The relative sensitivity to serum neutralization of VSV-G, Cocal, and RD114/TR pseudotyped lentiviral vectors was also compared in canines and macaques, two commonly used large animal models for preclinical gene therapy studies. Vector preparations were incubated with or without serum at 37° C. before 20 being plated onto cells, and the number of EGFP-transducing units remaining were determined relative to the vector-only control (FIG. 3). For Cocal and VSV-G pseudotypes the level of serum inactivation varied significantly between human individuals (p<0.0001). The level of serum resistance was not significantly different between individuals for RD114/TR (p=0.12). In humans, Cocal pseudotyped vector virions were overall relatively resistant to serum neutralization. In 7/10 individuals VSV-G pseudotyped vectors were neutralized significantly more than Cocal pseudotyped vectors (Pts. #2,3,5,6,9, p<0.01, Pts #7, 10 p<0.05). The RD|14/TR pseudotyped vector was inactivated more than Cocal pseudotyped vector in 6/10 individuals (Pts. #4,5,6,7,9,10). One individual's (Pt. #8) serum had a higher neutralizing activity to Cocal than VSV-G or RD114/TR but the difference was not significant (p=0.95 and p=0.31 respectively). Overall, these data suggest that Cocal pseudotyped vectors may be more effective than VSV-G or RD 114/TR pseudotyped vectors for in vivo delivery in humans, since they are more resistant to inactivation when incubated in human serum. The ability to produce Cocal pseudotyped vectors at approximately 100-fold higher titers than RD 114/TR pseudotypes (Table 1) should also be taken into consideration for in vivo applications.

The relative sensitivity to serum neutralization of VSV-G, Cocal and RD 114/TR pseudotyped lentiviral vectors was also compared in dogs, a commonly used large animal model for preclinical gene therapy studies. For all pseudotypes, the level of inactivation varied significantly between dogs ($p<0.001$ for RD114/TR and VSV-G and $p<0.05$ for Cocal). Canine serum potently inactivated both Cocal and VSV-G pseudotyped vectors, and RD114/TR was significantly more resistant than either Cocal or VSV-G ($p<0.01$) to inactivation in all 5 dogs (FIG. 3B).

We also compared neutralization of VSV-G and Cocal envelope pseudotyped vectors in five macaques (FIG. 3C). The level of inactivation varied significantly between animals for Cocal ($p<0.05$), but not for VSV-G ($p=0.95$) pseudotyped vectors. In 415 animals there was no significant difference in the level of inactivation for Cocal or VSV-G pseudotypes, and in one monkey VSV-G pseudotyped lentiviral vectors were more resistant to neutralization than Cocal pseudotyped vectors.

The Cocal envelope pseudotyped vector virions disclosed herein are resistant to inactivation when incubated with human serum in 70% of the patients tested. This suggests that Cocal pseudotyped vectors may be more effective for in vivo gene delivery in individuals having high levels of pre-existing serum neutralizing activity to VSV-G. Additionally, the unexpected observation that different individuals exhibit different pre-existing serum resistance to Cocal and VSV-G pseudotypes suggests that the selection of pseudotype for in vivo delivery can be tailored for a specific individual by performing a simple serum neutralization test prior to vector administration.

In canine and macaque serum, significant differences were observed in neutralization for Cocal and VSV-G pseudotypes. The RD 114/TR pseudotype was relatively resistant to neutralization in dog serum and may be better for in vivo delivery in this model. The lower titers obtained using RD 114/TR limit its utility for in vivo delivery applications requiring transduction of a large numbers of cells. The RD 114 pseudotype is effective for therapeutic delivery in the canine X-SCID setting using oncoretroviral vectors where corrected cells have a selective advantage and small numbers of transduced cells can expand and cure the disease phenotype. Ting-De Ravin et al., *Blood* 107:3091-3097 (2006).

Example 5

Efficient Transduction of Hematopoietic Progenitors with Cocal Pseudotyped Lentiviral Vectors Hematopoietic stem cells are an attractive target for gene therapy applications since these cells can be easily harvested and transduced ex vivo then reintroduced to reconstitute the entire hematopoietic system. Lentiviral vectors pseudotyped with VSV-G allow for efficient transduction of repopulating cells in nonobese-diabetic severe combined immunodeficient (NOD/SCID) xenotransplantation assays for human repopulating cells (Miyoshi et al., *Science* 283:682-686 (1999)) and in large animal models. Trobridge et al., *Blood* 111:5537-5543 (2008); Horn et al., *Blood* 103:3710-3716 (2004); and Hanawa et al., *Blood* 103:4062-4069 (2004). Lentiviral vectors pseudotyped with the RD 114/TR envelope efficiently transduce human and primate hematopoietic progenitor cells (Sandrin et al., *Blood* 100:823-832 (2002); Hanawa et al., *Mal. Ther:* 242-251 (2002)), and when directly compared at a similar MOI are more efficient for gene transfer to human CD34+ NOD/SCID repopulating cells than VSV-G. Di Nunzio et al., *Hum. Gene Ther:* 811-820 (2007).

The efficiency of transduction of CD34+ hematopoietic progenitors from humans, pigtailed macaques (*Macaca nemestrina*), and canines were compared using the three different envelope pseudotypes. Transduction was detected in CD34-derived cells in liquid culture by flow cytometry and also by visual scoring of EGFP-positive CPUs by fluorescent microscopy (FIG. 4). The Cocal envelope allowed for efficient transduction of hematopoietic progenitors from humans, macaques, and dogs. Analysis of the plating efficiency for all three pseudotypes were compared in triplicate at the same MOI (5) in human cultures and showed that there was no significant difference in the relative ability of hematopoietic progenitors to form colonies after exposure to vector preparations ($p=0.12$). Thus, there was no difference in toxicity to hematopoietic progenitors between vector preparations of the different pseudotypes. Transduction of pigtailed macaque CD34+ cells with the Cocal envelope was slightly more efficient than with VSV-G or RD|14/TR when compared at the same MOI, similar to what was observed in pigtailed macaque stromal cells and skin fibroblasts. Together, these data demonstrate that Cocal pseudotyped lentiviral vectors efficiently transduced hematopoietic progenitor cells, suggesting that they may be highly effective for HSC gene therapy.

Example 6

Efficient Transduction of Pigtailed Macaque Repopulating Cells with Cocal Pseudotyped Lentiviral Vectors Given the high efficiency of transduction of macaque and human hematopoietic progenitors using Cocal pseudotyped vectors, the relative ability of Cocal and VSV-G pseudotyped vectors to transduce long-term repopulating cells was compared in a clinically relevant nonhuman primate model. A competitive repopulation model was employed to directly compare transduction and engraftment of VSV-G and Cocal pseudotyped lentiviral vectors in the same animal. In this approach, a lentiviral EGFP vector was pseudotyped with VSV-G, and a second lentiviral vector that expresses enhanced yellow fluorescent protein (EYFP) reporter gene was pseudotyped with Cocal envelope. The green and yellow proteins differ only by five amino acids and are thus immunologically highly similar. Repopulating cells expressing these fluorophores can be easily distinguished and accurately quantitated in vivo by flow cytometry. CD34+ cells were transduced separately at an MOI of 20 using each pseudotype, extensively washed, and then sequentially infused into a myeloblated (1020 cGy total body irradiation) macaque. Using this approach, hematopoietic repopulating cells could be transduced by either the EGFP-expressing Cocal pseudotyped vector or the EYFP-expressing VSV-G pseudotyped vector, but not both. Analysis of pretransplant marking showed approximately 4.5-fold higher marking in the Cocal arm in liquid cultures at day 11 post-vector exposure and marking in CPUs was similar to these results in liquid cultures (Table 2).

TABLE 2

Pre-infusion Transduction Efficiency and Engraftment of Pigtailed Macaque CD34+ Cells

| Monkey* | CD34+ Purity | No. of CD34-enriched cells/ kg × 10$^6$ before culture | Envelope Glycoprotein/ Fluorophore | No. of Infused Cells/ kg × 10$^6$ | MOI** | Pre-infusion Transduction Efficiency*** | Days to ANC > 500 | Days to Platelets > 20,000 |
|---|---|---|---|---|---|---|---|---|
| L06348 (2.8 kg) | 99% | 7.1 | Cocal/EGFP | 41 | 20 | 17%, 17% | 14 | 25 |
|  |  | 7.1 | VSV- G/EGFP | 32 | 20 | 3.8%, 5% |  |  |

Figure 5:
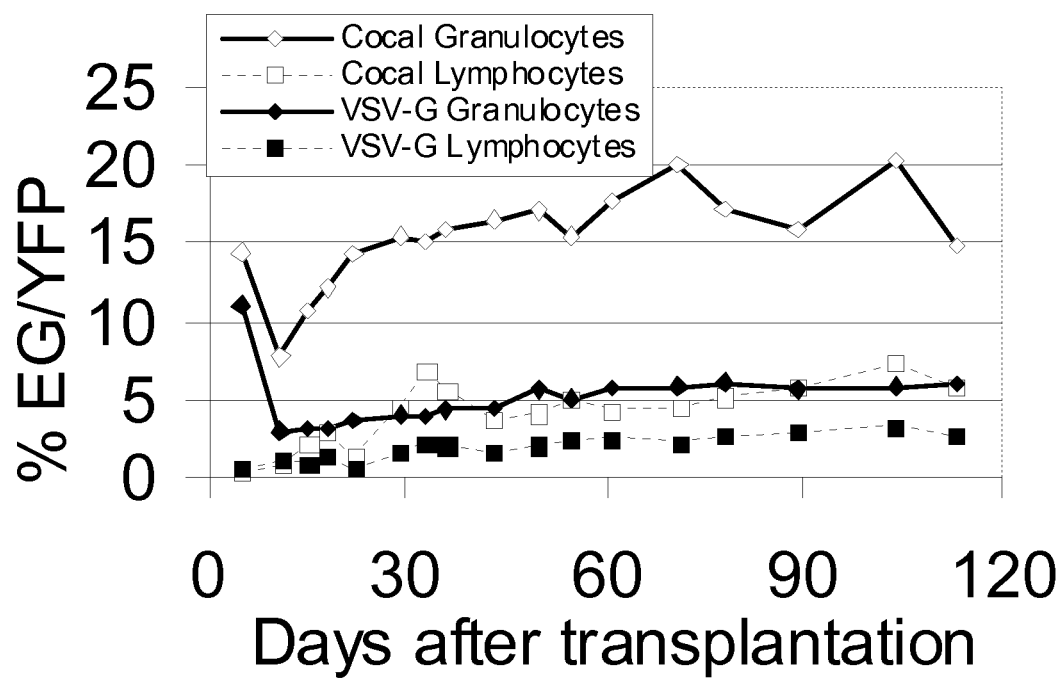
FIG. 5. Engraftment and transgene expression levels in peripheral blood cells of a pigtailed macaque that received both Cocal and VSV-G pseudotyped lentivirally transduced stem cells. The percentages of EGFP (Cocal) and Enhanced Yellow Fluorescent Protein (EYFP; VSV-G)-expressing leukocytes in the peripheral blood detected by flow-cytometry are shown.

*Monkey and weight at time of transplantation in brackets
**Multiplicity of infection based on titer determined by transduction of HT 1080 cells
***Percentage of fluorescence-positive cells assessed y flow cytometry for EGFP or EYFP in liquid cultures on day 11 after transduction, and percentage of fluorescence-positive colony forming units Engraftment was rapid with 14 days to an ANC greater than 500/μl and 25 days to a platelet count greater than 50,000/μl. Transduced cells in the peripheral blood were then quantitated in vivo by flow cytometry (FIG. 5). The data demonstrated that the Cocal pseudotyped vector allowed for highly efficient gene transfer with up to 20% marking as assessed by transgene expression in granulocytes and 6% in lymphocytes. Marking in this animal as assessed by transgene expression was approximately 2.8-fold higher for the Cocal arm than for the VSV-G arm in granulocytes and 2.2-fold higher in lymphocytes.

At a relatively low MOI (5), lentiviral vectors pseudotyped with Cocal envelope consistently transduce pigtailed macaque cells more efficiently than VSV-G pseudotyped vectors while exhibiting similar transduction efficiency in human cells. The transduction efficiency in pigtailed macaque cells closely reflects the efficiency in human cells, suggesting that Cocal envelope may be a better pseudotype than VSV-G for gene transfer studies in the pigtailed macaque model, since it may be more predictive of gene transfer in patients.

Nonhuman primates are particularly useful for HSC gene therapy since primates very closely model hematopoiesis in humans. The pigtailed macaque in particular is an excellent model to evaluate HIV-based lentiviral vector transduction because, unlike rhesus macaques, pigtailed macaque repopulating cells can be efficiently transduced using VSV-G pseudotyped HIV-based vectors that also efficiently transduce human cells. Trobridge et al., Blood 111:5537-5543 (2008). Transduction of HSCs is limited by several factors which include the quiescence of target long-term repopulating cells, but also the availability of the host envelope receptor that mediates efficient entry of viral vectors. Sabatino et al., Blood Cells, Molecules, and Diseases 23:422-433 (1997) and Kurre et al., J Virol. 73:495-500 (1999).

As part of the present disclosure, higher marking in macaque repopulating cells using the Cocal pseudotyped vectors was observed up to 113 days post-transplant. Marking will be monitored longer term (>1 year) to determine if there are any obvious differences between VSV-G and Cocal envelope in lineage marking of longer-term repopulating cells. Cocal envelope can mediate efficient multi-lineage gene transfer to macaque long-term (>90 days) repopulating cells. Additional studies are performed to confirm that Cocal pseudotyped vectors are more efficient than VSV-G for HSC gene
transfer in this model.

Example 7

Pseudotyping Gammaretroviral Vectors

Figure 11:
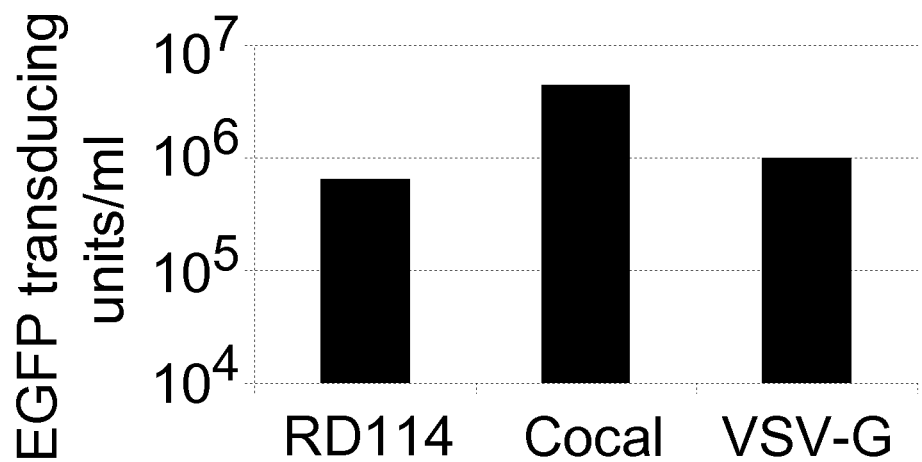
FIG. 11. Pseudotyping gammaretroviral vectors. The titers of a Moloney leukemia virus-based vector expressing EGFP by co-transfection of cocal, VSV, and RD 114/TR envelope glycoproteins are compared.

A Moloney leukemia virus-based vector that expresses EGFP was produced by transient transfection with cocal, VSV, and RDI14/TR envelope glycoproteins, the vector supernatants were concentrated by centrifugation and the titers were compared (FIG. 11). Cocal was found to efficiently pseudotype gammaretroviral vectors and to allow concentration of these vectors. These data extend the use of cocal envelope for use with gammaretroviral vectors, and suggests it may be a versatile envelope for additional enveloped vector types.

Example 8

Figure 12:
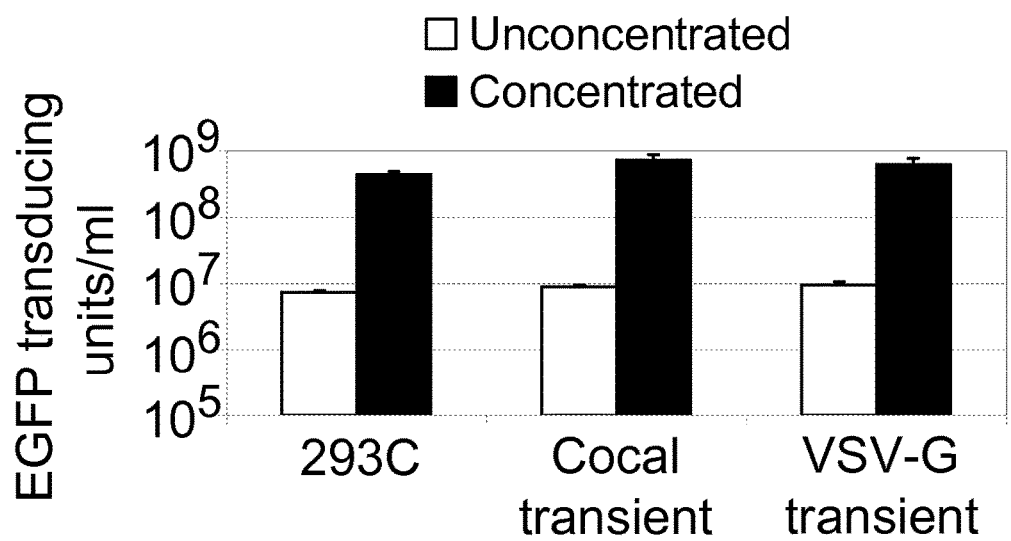
FIG. 12. Efficient production of lentiviral vectors from 293C cells.

Production of a Human Embryonic Kidney 293C Packaging Cell that Constitutively Produces Cocal Envelope One limitation of the VSV-G envelope is that it is difficult to produce high-titer packaging cells that constitutively express VSV-G. To generate a packaging cell that would constitutively produce cocal envelope, human embryonic kidney 293 cells were transfected with the cocal envelope plasmid and with a plasmid that expresses a blasticidin resistance gene. Blasticidin-resistant colonies were isolated and each individual cell line was screened for their ability to stably produce cocal envelope using an EGFP-expressing vector. A packaging cell was identified (named 293C for 293 Cocal) that constitutively produces cocal envelope as evidenced by the ability to produce high titer lentiviral vector when transfected with vector and helper plasmids in the absence of an envelope plasmid. This 293C cell line produced high titer lentiviral vector (FIG. 12) that can be efficiently concentrated by centrifugation. 293C shows vector made from the 293C cell line, the 'Cocal transient' and 'VSV-G transient' controls show vector made from transiently co-transfecting cocal and VSV-G envelope plasmids into 293 cells. This cell line was generated from a single colony and cultured and expanded for over 6 weeks, so expression of the cocal envelope is stable. This 293C packaging cell line may have broad utility for the production of many types of viral vectors including vectors for gene therapy and for vaccines. Vector producing cells may be generated using this 293C packaging line.

Example 9

Production of a Phoenix-Cocal Packaging Cell that Constitutively Produces Cocal Envelope and Also Gammaretroviral Gag and Pol Phoenix packaging cells developed by Garry Nolan's research group express gammaretroviral Gag and Pol and produce vector virions when transfected with a gammaretroviral vector and envelope plasmids. Phoenix packaging cells were transfected with the cocal envelope plasmid and a blasticidin-resistance plasmid. Stable blasticidin-resistant Phoenix-derived colonies that expressed cocal and produce vector were screened for their ability to produce cocal-pseudotyped EFGP-expressing vector.

One cell line (named Phoenix-C for Phoenix-Cocal) was identified that produced high titer gammaretroviral vector when transfected with a vector plasmid only. This cell line was generated from a single colony and cultured and expanded for over 6 weeks to ensure stable expression of the cocal envelope. For this Phoenix-C packaging line, concentrated gammaretroviral vector stocks of over $10^6$ EGFP transducing units/ml were generated.

Example 10

Transduction of Long Term (>1 Year) Repopulating Cells in a Nonhuman Primate Model Cocal-pseudotyped vectors have been shown to be capable of efficiently transducing pigtailed macaque (*Macaca nemestrina*) hematopoietic repopulating cells.

Figure 13:
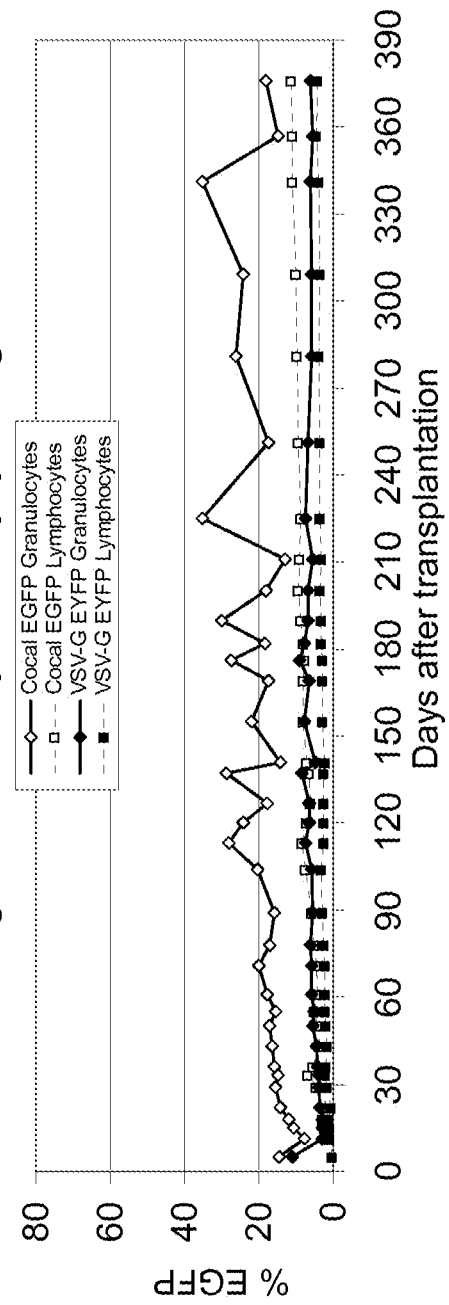
FIG. 13. Efficient marking in nonhuman primate long term hematopoietic repopulating cells.

Marking to over 1 year has been demonstrated in this animal. Marking was compared using a competitive repopulation assay with EGFP (cocal) and EYFP (VSV-G) experimental arms. After 1 year, marking in the cocal arm remained higher than the VSV-G arm in both myeloid and lymphoid cells. These data showed that cocal envelope could mediate efficient gene transfer to long term repopulating cells in a clinically relevant large animal model. See FIG. 13

Example 11

Generation of a Gammaretroviral Producer Cell Line Based on the Phoenix-Cocal Packaging Cell The Phoenix-cocal packaging cell was transfected with a gammaretroviral vector plasmid (pMND-EGFP-SN−/−) and a puromycin resistance plasmid pPur. Puromycin-resistant colonies were screened for production of EGFP-expressing vector. A stable producer line was obtained that stably produces the gammaretroviral vector after over 5 weeks in culture. The vector from this stable producer cell line was concentrated 100-fold by centrifugation to a titer of $7.2\times10^7$ EGFP transducing units/ml. High-titer gammaretroviral producer cell lines were generated that stably expressed cocal envelope allowing for the production of vectors in the cell supernatant that can be efficiently concentrated to high titer. This also suggests that stable cocal-pseudotyped producer cell lines can be generated for other vector types including lentiviral vectors. Cocal pseudotyped producer cells can be used for many scientific and therapeutic applications including gene therapy and the production of reprogramming vectors to generate induced pluripotent stem cells for broad application in regenerative medicine.

What is claimed is:

1. A polynucleotide comprising a human codon-optimized nucleotide sequence encoding a Cocal vesiculovirus envelope protein wherein the polynucleotide comprises SEQ ID NO: 3.

2. The polynucleotide of claim 1 under transcriptional control of a eukaryotic transcriptional promoter.

3. The polynucleotide of claim 2 wherein the eukaryotic transcriptional promoter comprises a cytomegalovirus (CMV) promoter.

4. A plasmid vector for the expression of a Cocal vesiculovirus envelope protein, the plasmid vector comprising SEQ ID NO: 3.

5. The plasmid vector of claim 4 further comprising a eukaryotic transcriptional promoter.

6. The plasmid vector of claim 5 wherein the eukaryotic transcriptional promoter comprises a CMV promoter.

7. The plasmid vector of claim 6 further comprising a human beta-globin intron between the CMV promoter and the polynucleotide comprising SEQ ID NO: 3.

8. The plasmid vector of claim 6 further comprising a polyadenylation signal.

9. A cell comprising a polynucleotide comprising SEQ ID NO: 3.

10. The cell of claim 9, wherein the polynucleotide is under transcriptional control of a eukaryotic transcriptional promoter.

11. The cell of claim 9 comprising a plasmid vector for the expression of a Cocal vesiculovirus envelope protein, the plasmid vector comprising SEQ ID NO: 3.

12. The cell of claim 9 wherein the cell is a human embryonic kidney (HEK) 293 cell, a HT1080 fibrosarcoma cell, or a CD34+ hematopoietic progenitor cell.

13. The cell of claim 9 comprising a retroviral vector.

14. The cell of claim 13 wherein the retroviral vector comprises a lentiviral vector.

15. The cell of claim 13 wherein the retroviral vector comprises a gammaretroviral vector.

16. The cell of claim 13 comprising a retroviral helper plasmid.

* * * * *

SEQUENCE LISTING

```
<160> NUMBER OF SEQ ID NOS: 5

<210> SEQ ID NO 1
<211> LENGTH: 1652
<212> TYPE: DNA
<213> ORGANISM: Cocal Vesiculovirus

<400> SEQUENCE: 1
aacagtgatc aactgttcca gattcaacat gaatttccta ctcttgacat ttattgtgtt     60
gccgttgtgc agccacgcca agttctccat tgtattccct caaagccaaa aaggcaattg    120
gaagaatgta ccatcatctt accattactg cccttcaagt tcggatcaaa actggcacaa    180
tgatttgctt ggaatcacaa tgaaagtcaa aatgcccaaa acacacaaag ctattcaagc    240
agacgggtgg atgtgtcatg ctgccaaatg gatcactacc tgtgactttc gctggtacgg    300
acccaaatac atcactcact ccattcattc catccagcct acttcagagc agtgtaaaga    360
aagcatcaag caaacaaaac aaggtacttg gatgagtcct ggcttccctc cacagaactg    420
cgggtatgca acagtaacag actctgtcgc tgttgtcgtc caagccactc ctcatcatgt    480
cttggttgat gaatatactg gagaatggat cgactctcaa ttccccaacg ggaaatgtga    540
aaccgaagag tgcgagaccg tccacaactc taccgtatgg tactctgact acaaagtaac    600
tggattatgt gacgcaactc tggtagacac agagatcacc ttcttctctg aagatggcaa    660
aaaagaatct atcgggaagc ccaacacagg ctataggagc aactacttcg cttatgagaa    720
aggggacaaa gtatgtaaaa tgaactactg caagcatgcg ggtgtgaggt tgccttccgg    780
ggtttggttt gagtttgtgg atcaggatgt ctacgccgcc gccaaacttc cagaatgccc    840
cgttggtgcc actatctccg ctccgacaca gacctctgtt gacgtaagtc tcattctaga    900
tgtagagaga attttagatt actctctgtg tcaagagaca tggagcaaga tccggtccaa    960
acagccagta tcccctgttg accttagtta cttggccccc aagaatcctg ggaccggacc   1020
ggcattcaca atcatcaatg gcactctgaa gtactttgag accagataca ttcggattga   1080

-continued

```
tatagacaat ccaatcatct ccaagatggt ggggaaaata agtggcagtc aaacagaacg    1140
agaattgtgg acagagtggt tcccctacga gggtgtcgag atagggccaa atgggattct    1200
caaaacccct acaggataca aattcccact cttcatgata ggacacggga tgctagattc    1260
cgacttgcac aagacgtccc aagcagaggt ctttgaacat cctcaccttg cagaagcacc    1320
aaagcagttg ccggaggagg agactttatt ttttggtgac acaggaatct ccaaaaatcc    1380
ggtcgaactg attgaaggt ggtttagtag ttggaagagc actgtagtca cctttttctt    1440
tgccatagga gtatttatac tactgtatgt agtggccaga attgtgatcg cagtgagata    1500
cagatatcaa ggctcaaata acaaaagaat ttacaatgat attgagatga gcagatttag    1560
aaaatgatga agaccctcag atgattatac atatgtgata tgaaaaaaac taacagtcat    1620
catggacttg aatgacttcg agttgagaca gt                                  1652
```

<210> SEQ ID NO 2
<211> LENGTH: 512
<212> TYPE: PRT
<213> ORGANISM: Cocal Vesiculovirus

<400> SEQUENCE: 2

```
Met Asn Phe Leu Leu Thr Phe Ile Val Leu Pro Leu Cys Ser His
 1

```
Gly Ala Thr Ile Ser Ala Pro Thr Gln Thr Ser Val Asp Val Ser Leu
            275                 280                 285

Ile Leu Asp Val Glu Arg Ile Leu Asp Tyr Ser Leu Cys Gln Glu Thr
        290                 295                 300

Trp Ser Lys Ile Arg Ser Lys Gln Pro Val Ser Pro Val Asp Leu Ser
305                 310                 315                 320

Tyr Leu Ala Pro Lys Asn Pro Gly Thr Gly Pro Ala Phe Thr Ile Ile
                325                 330                 335

Asn Gly Thr Leu Lys Tyr Phe Glu Thr Arg Tyr Ile Arg Ile Asp Ile
            340                 345                 350

Asp Asn Pro Ile Ile Ser Lys Met Val Gly Lys Ile Ser Gly Ser Gln
        355                 360                 365

Thr Glu Arg Glu Leu Trp Thr Glu Trp Phe Pro Tyr Glu Gly Val Glu
    370                 375                 380

Ile Gly Pro Asn Gly Ile Leu Lys Thr Pro Thr Gly Tyr Lys Phe Pro
385                 390                 395                 400

Leu Phe Met Ile Gly His Gly Met Leu Asp Ser Asp Leu His Lys Thr
                405                 410                 415

Ser Gln Ala Glu Val Phe Glu His Pro His Leu Ala Glu Ala Pro Lys
            420                 425                 430

Gln Leu Pro Glu Glu Glu Thr Leu Phe Phe Gly Asp Thr Gly Ile Ser
        435                 440                 445

Lys Asn Pro Val Glu Leu Ile Glu Gly Trp Phe Ser Ser Trp Lys Ser
    450                 455                 460

Thr Val Val Thr Phe Phe Pro Ala Ile Gly Val Phe Ile Leu Leu Tyr
465                 470                 475                 480

Val Val Ala Arg Ile Val Ile Ala Val Arg Tyr Arg Tyr Gln Gly Ser
                485                 490                 495

Asn Asn Lys Arg Ile Tyr Asn Asp Ile Glu Met Ser Arg Phe Arg Lys
            500                 505                 510
```

<210> SEQ ID NO 3
<211> LENGTH: 1539
<212> TYPE: DNA
<213> ORGANISM: Cocal Vesiculovirus

<400> SEQUENCE: 3

```
atgaattttc ttctcttgac ctttatcgtc cttccgctct gcagtcacgc taaattttcg      60
atcgtcttcc cacagagtca gaagggcaat tggaagaatg taccgagttc atatcattat     120
tgtccaagca gctctgatca aaactggcat aacgacctgc tgggcattac catgaaggtg     180
aaaatgccta agacacataa ggcgattcag gcagacgggt ggatgtgcca cgcagccaag     240
tggattacaa cttgtgactt ccgatggtac ggtcctaagt atattactca ctccatacac     300
agcatccagc ccaccagtga gcagtgcaaa gagagtatca agcagaccaa gcagggaacc     360
tggatgtcac ctggctttcc acctcagaat tgtggctatg caacagtgac agactcagtg     420
gctgttgtgg tgcaggcaac cccccaccac gtactcgttg acgaatatac aggcgaatgg     480
attgactccc agtttcccaa cggtaaatgc gagacagaag agtgcgagac tgtgcacaat     540
tcaacagtgt ggtactccga ttataaggtt accgggcttt cgacgccac actggtggac      600
acagagataa cgttttttc cgaagacgga aaaaggaaa gtatcgggaa acccaacact       660
ggataccgga gcaattactt cgcgtatgag aaaggagata ggtctgcaa atgaattat       720
tgcaaacacg ccggggtaag gctgccctcc ggcgtgtggt ttgagttcgt ggaccaggac     780
```

```
gtctacgcag ccgccaaatt gcccgagtgt ccagtgggag ctacaatttc cgcaccgaca    840
caaacctcag tggatgtgtc tctgattctg acgtagaga ggatcctcga ctactctttg     900
tgtcaggaga cgtggagcaa gatacggtct aagcaaccag tctcacccgt agatttgagc    960
tacctcgccc cgaaaaaccc aggcacgggc ccagcgttca cgatcatcaa cggcacgctt   1020
aaatatttcg agactcgcta tatccgcatc gacatcgaca atcctatcat ctctaagatg   1080
gtgggtaaga tctctggatc ccagactgaa cgagaactgt ggacagaatg gttccctac    1140 gagggcgtcg agattggccc taacggaata ctgaagaccc ctaccggcta taagttccct   1200
ctgtttatga tcggcacgg aatgctggat tctgatttgc ataagacttc acaagcagaa    1260
gtctttgaac atcctcacct cgccgaagca cctaaacagt tgcctgagga agagaccctg   1320
ttcttcggcg atacaggtat atccaaaaac ccggtggagc ttatcgaagg ttggtttagc   1380
agctggaagt caacagtggt aactttcttc ttcgccatcg gcgtgtttat acttctgtac   1440
gtagtggccc gcatcgtgat cgcagtgcgc tacagatacc aaggaagcaa caacaaaaga   1500
atctacaacg acatagagat gagccgcttc aggaagtga                           1539
```

<210> SEQ ID NO 4
<211> LENGTH: 512
<212> TYPE: PRT
<213> ORGANISM: Cocal Vesiculovirus

<400> SEQUENCE: 4

```
Met Asn Phe Leu Leu Thr Phe Ile Val Leu Pro Leu Cys Ser His
1               5                   10                  15

Ala Lys Phe Ser Ile Val Phe Pro Gln Ser Gln Lys Gly Asn Trp Lys
                20                  25                  30

Asn Val Pro Ser Ser Tyr His Tyr Cys Pro Ser Ser Asp Gln Asn
            35                  40                  45

Trp His Asn Asp Leu Leu Gly Ile Thr Met Lys Val Lys Met Pro Lys
    50                  55                  60

Thr His Lys Ala Ile Gln Ala Asp Gly Trp Met Cys His Ala Ala Lys
65                  70                  75                  80

Trp Ile Thr Thr Cys Asp Phe Arg Trp Tyr Gly Pro Lys Tyr Ile Thr
                85                  90                  95

His Ser Ile His Ser Ile Gln Pro Thr Ser Glu Gln Cys Lys Glu Ser
            100                 105                 110

Ile Lys Gln Thr Lys Gln Gly Thr Trp Met Ser Pro Gly Phe Pro Pro
        115                 120                 125

Gln Asn Cys Gly Tyr Ala Thr Val Thr Asp Ser Val Ala Val Val
    130                 135                 140

Gln Ala Thr Pro His His Val Leu Val Asp Glu Tyr Thr Gly Glu Trp
145                 150                 155                 160

Ile Asp Ser Gln Phe Pro Asn Gly Lys Cys Glu Thr Glu Glu Cys Glu
                165                 170                 175

Thr Val His Asn Ser Thr Val Trp Tyr Ser Asp Tyr Lys Val Thr Gly
            180                 185                 190

Leu Cys Asp Ala Thr Leu Val Asp Thr Glu Ile Thr Phe Phe Ser Glu
        195                 200                 205

Asp Gly Lys Lys Glu Ser Ile Gly Lys Pro Asn Thr Gly Tyr Arg Ser
    210                 215                 220

Asn Tyr Phe Ala Tyr Glu Lys Gly Asp Lys Val Cys Lys Met Asn Tyr
225                 230                 235                 240
```

Cys Lys His Ala Gly Val Arg Leu Pro Ser Gly Val Trp Phe Glu Phe
                245                 250                 255

Val Asp Gln Asp Val Tyr Ala Ala Ala Lys Leu Pro Glu Cys Pro Val
            260                 265                 270

Gly Ala Thr Ile Ser Ala Pro Thr Gln Thr Ser Val Asp Val Ser Leu
        275                 280                 285

Ile Leu Asp Val Glu Arg Ile Leu Asp Tyr Ser Leu Cys Gln Glu Thr
    290                 295                 300

Trp Ser Lys Ile Arg Ser Lys Gln Pro Val Ser Pro Val Asp Leu Ser
305                 310                 315                 320

Tyr Leu Ala Pro Lys Asn Pro Gly Thr Gly Pro Ala Phe Thr Ile Ile
                325                 330                 335

Asn Gly Thr Leu Lys Tyr Phe Glu Thr Arg Tyr Ile Arg Ile Asp Ile
            340                 345                 350

Asp Asn Pro Ile Ile Ser Lys Met Val Gly Lys Ile Ser Gly Ser Gln
        355                 360                 365

Thr Glu Arg Glu Leu Trp Thr Glu Trp Phe Pro Tyr Glu Gly Val Glu
    370                 375                 380

Ile Gly Pro Asn Gly Ile Leu Lys Thr Pro Thr Gly Tyr Lys Phe Pro
385                 390                 395                 400

Leu Phe Met Ile Gly His Gly Met Leu Asp Ser Asp Leu His Lys Thr
                405                 410                 415

Ser Gln Ala Glu Val Phe Glu His Pro His Leu Ala Glu Ala Pro Lys
            420                 425                 430

Gln Leu Pro Glu Glu Thr Leu Phe Phe Gly Asp Thr Gly Ile Ser
        435                 440                 445

Lys Asn Pro Val Glu Leu Ile Glu Gly Trp Phe Ser Ser Trp Lys Ser
    450                 455                 460

Thr Val Val Thr Phe Phe Ala Ile Gly Val Phe Ile Leu Leu Tyr
465                 470                 475                 480

Val Val Ala Arg Ile Val Ile Ala Val Arg Tyr Arg Tyr Gln Gly Ser
                485                 490                 495

Asn Asn Lys Arg Ile Tyr Asn Asp Ile Glu Met Ser Arg Phe Arg Lys
            500                 505                 510

<210> SEQ ID NO 5
<211> LENGTH: 5722
<212> TYPE: DNA
<213> ORGANISM: Artificial Sequence
<220> FEATURE:
<223> OTHER INFORMATION: Lentiviral Vector pMD2.CocalG Nucleotide
      Sequence

<400> SEQUENCE: 5
ggatcccctg agggggcccc catgggctag aggatccggc ctcggcctct gcataaataa      60
aaaaaattag tcagccatga gcttggccca ttgcatacgt tgtatccata tcataatatg     120
tacatttata ttggctcatg tccaacatta ccgccatgtt gacattgatt attgactagt     180
tattaatagt aatcaattac ggggtcatta gttcatagcc catatatgga gttccgcgtt     240
acataactta cggtaaatgg cccgcctggc tgaccgccca acgacccccg cccattgacg     300
tcaataatga cgtatgttcc catagtaacg ccaatagggg ctttccattg acgtcaatgg     360
gtggagtatt tacggtaaac tgcccacttg gcagtacatc aagtgtatca tatgccaagt     420
acgcccccta ttgacgtcaa tgacggtaaa tggcccgcct ggcattatgc ccagtacatg     480

```
accttatggg actttcctac ttggcagtac atctacgtat tagtcatcgc tattaccatg      540
gtgatgcggt tttggcagta catcaatggg cgtggatagc ggtttgactc acggggattt      600
ccaagtctcc accccattga cgtcaatggg agtttgtttt ggcaccaaaa tcaacgggac      660
tttccaaaat gtcgtaacaa ctccgcccca ttgacgcaaa tgggcggtag gcgtgtacgg      720
tgggaggtct atataagcag agctcgttta gtgaaccgtc agatcgcctg gagacgccat      780
ccacgctgtt tgacctccca tagaagacac cgggaccgat ccagcctccc ctcgaagctt      840
acatgtggta ccgagctcgg atcctgagaa cttcagggtg agtctatggg acccttgatg      900
ttttctttcc ccttcttttc tatggttaag ttcatgtcat aggaagggga gaagtaacag      960
ggtacacata ttgaccaaat cagggtaatt ttgcatttgt aattttaaaa aatgctttct     1020
tcttttaata tacttttttg tttatcttat ttctaatact ttccctaatc tctttctttc     1080
agggcaataa tgatacaatg tatcatgcct ctttgcacca ttctaaagaa taacagtgat     1140
aatttctggg ttaaggcaat agcaatattt ctgcatataa atatttctgc atataaattg     1200
taactgatgt aagaggtttc atattgctaa tagcagctac aatccagcta ccattctgct     1260
tttattttat ggttgggata aggctggatt attctgagtc caagctaggc ccttttgcta     1320
atcatgttca tacctcttat cttcctccca cagctcctgg gcaacgtgct ggtctgtgtg     1380
ctggcccatc actttggcaa agcacgtgag atctgaattc atcgatgcgg ccgccaccat     1440
gaattttctt ctcttgacct ttatcgtcct tccgctctgc agtcacgcta aattttcgat     1500
cgtcttccca cagagtcaga agggcaattg gaagaatgta ccgagttcat atcattattg     1560
tccaagcagc tctgatcaaa actggcataa cgacctgctg gcattaccca tgaaggtgaa     1620
aatgcctaag acacataagg cgattcaggc agacgggtgg atgtgccacg cagccaagtg     1680
gattacaact tgtgacttcc gatggtacgg tcctaagtat attactcact ccatacacag     1740
catccagccc accagtgagc agtgcaaaga gagtatcaag cagaccaagc agggaacctg     1800
gatgtcacct ggctttccac ctcagaattg tggctatgca acagtgacag actcagtggc     1860
tgttgtggtg caggcaaccc cccaccacgt actcgttgac gaatatacag gcgaatggat     1920
tgactcccag tttcccaacg gtaaatgcga gacagaagag tgcgagactg tgcacaattc     1980
aacagtgtgg tactccgatt ataaggttac cgggctttgc gacgccacac tggtggacac     2040
agagataacg ttttttttccg aagacggaaa aaaggaaagt atcgggaaac caacactgg      2100 ataccggagc aattacttcg cgtatgagaa aggagataag gtctgcaaaa tgaattattg     2160 caaaacacgcc ggggtaaggc tgccctccgg cgtgtggttt gagttcgtgg accaggacgt    2220
ctacgcagcc gccaaattgc ccgagtgtcc agtgggagct acaatttccg caccgacaca    2280
aacctcagtg gatgtgtctc tgattctgga cgtagagagg atcctcgact actcttttgtg   2340 tcaggagacg tggagcaaga tacggtctaa gcaaccagtc tcacccgtag atttgagcta    2400
cctcgccccg aaaaacccag gcacgggccc agcgttcacg atcatcaacg gcacgcttaa    2460
atatttcgag actcgctata tccgcatcga catcgacaat cctatcatct ctaagatggt    2520
gggtaagatc tctggatccc agactgaacg agaactgtgg acagaatggt tccctacga    2580 gggcgtcgag attggcccta acggaatact gaagaccccct accggctata agttccctct  2640
gtttatgatc ggccacggaa tgctggattc tgatttgcat aagacttcac aagcagaagt    2700
ctttgaacat cctcacctcg ccgaagcacc taaacagttg cctgaggaag agaccctgtt    2760
cttcggcgat acaggtatat ccaaaaaccc ggtggagctt atcgaaggtt ggtttagcag    2820
ctggaagtca acagtggtaa cttttcttctt cgccatcggc gtgtttatac ttctgtacgt   2880
```

```
agtggcccgc atcgtgatcg cagtgcgcta cagataccaa ggaagcaaca acaaaagaat    2940
ctacaacgac atagagatga gccgcttcag gaagtgaagg cctgaattca ccccaccagt    3000
gcaggctgcc tatcagaaag tggtggctgg tgtggctaat gccctggccc acaagtttca    3060
ctaagctcgc ttccttgctg tccaatttct attaaaggtt ccttggttcc ctaagtccaa    3120
ctactaaact gggggatatt atgaagggcc ttgagcatct ggattctgcc taataaaaaa    3180
catttatttt cattgcaatg atgtatttaa attatttctg aatattttac taaaagggga    3240
atgtgggagg tcagtgcatt taaaacataa agaaatgaag agctagttca aaccttggga    3300
aaatacacta tatcttaaac tccatgaaag aaggtgaggc tgcaaacagc taatgcacat    3360
tggcaacagc cctgatgcct atgccttatt catccctcag aaaaggattc aagtagaggc    3420
ttgatttgga ggttaaagtt tggctatgct gtattttaca ttacttattg ttttagctgt    3480
cctcatgaat gtcttttcac tacccatttg cttatcctgc atctctcagc cttgactcca    3540
ctcagttctc ttgcttagag ataccacctt tcccctgaag tgttccttcc atgttttacg    3600
gcgagatggt ttctcctcgc ctggccactc agccttagtt gtctctgttg tcttatagag    3660
gtctacttga agaaggaaaa acaggggggca tggtttgact gtcctgtgag cccttcttcc    3720
ctgcctcccc cactcacagt gacccggaat ccctcgacat ggcagtctag cactagtgcg    3780
gccgcagatc tgcttcctcg ctcactgact cgctgcgctc ggtcgttcgg ctgcggcgag    3840
cggtatcagc tcactcaaag gcggtaatac ggttatccac agaatcaggg gataacgcag    3900
gaaagaacat gtgagcaaaa ggccagcaaa aggccaggaa ccgtaaaaag gccgcgttgc    3960
tggcgttttt ccataggctc cgcccccctg acgagcatca caaaaatcga cgctcaagtc    4020
agaggtggcg aaacccgaca ggactataaa gataccaggc gtttccccct ggaagctccc    4080
tcgtgcgctc tcctgttccg accctgccgc ttaccggata cctgtccgcc tttctccctt    4140
cgggaagcgt ggcgctttct caatgctcac gctgtaggta tctcagttcg gtgtaggtcg    4200
ttcgctccaa gctgggctgt gtgcacgaac ccccccgttca gcccgaccgc tgcgccttat    4260
ccggtaacta tcgtcttgag tccaacccgg taagacacga cttatcgcca ctggcagcag    4320
ccactggtaa caggattagc agagcgaggt atgtaggcgg tgctacagag ttcttgaagt    4380
ggtggcctaa ctacggctac actagaagga cagtatttgg tatctgcgct ctgctgaagc    4440
cagttacctt cggaaaaaga gttggtagct cttgatccgg caaacaaacc accgctggta    4500
gcggtggttt ttttgtttgc aagcagcaga ttacgcgcag aaaaaaagga tctcaagaag    4560
atcctttgat cttttctacg gggtctgacg ctcagtggaa cgaaaactca cgttaaggga    4620
ttttggtcat gagattatca aaaaggatct tcacctagat ccttttaaat taaaaatgaa    4680
gttttaaatc aatctaaagt atatatgagt aaacttggtc tgacagttac caatgcttaa    4740
tcagtgaggc acctatctca gcgatctgtc tatttcgttc atccatagtt gcctgactcc    4800
ccgtcgtgta gataactacg atacgggagg gcttaccatc tggccccagt gctgcaatga    4860
taccgcgaga cccacgctca ccggctccag atttatcagc aataaaccag ccagccggaa    4920
gggccgagcg cagaagtggt cctgcaactt tatccgcctc catccagtct attaattgtt    4980
gccgggaagc tagagtaagt agttcgccag ttaatagttt cgcaacgtt gttgccattg    5040 ctacaggcat cgtggtgtca cgctcgtcgt ttggtatggc ttcattcagc tccggttccc    5100
aacgatcaag gcgagttaca tgatccccca tgttgtgcaa aaaagcggtt agctccttcg    5160
gtcctccgat cgttgtcaga agtaagttgg ccgcagtgtt atcactcatg gttatggcag    5220
```

```
cactgcataa ttctcttact gtcatgccat ccgtaagatg cttttctgtg actggtgagt    5280
actcaaccaa gtcattctga gaatagtgta tgcggcgacc gagttgctct tgcccggcgt    5340
caatacggga taataccgcg ccacatagca gaactttaaa agtgctcatc attggaaaac    5400
gttcttcggg gcgaaaactc tcaaggatct taccgctgtt gagatccagt tcgatgtaac    5460
ccactcgtgc acccaactga tcttcagcat ctttactttt caccagcgtt tctgggtgag    5520
caaaaacagg aaggcaaaat gccgcaaaaa agggaataag ggcgacacgg aaatgttgaa    5580
tactcatact cttcctttt caatattatt gaagcattta tcagggttat tgtctcatga    5640
gcggatacat atttgaatgt atttagaaaa ataaacaaat aggggttccg cgcacatttc    5700
cccgaaaagt gccacctgac gt                                            5722
```